US010966857B2

(12) United States Patent
Gaylord

(10) Patent No.: US 10,966,857 B2
(45) Date of Patent: Apr. 6, 2021

(54) WRIST BRACE WITH ENHANCED LACING

(71) Applicant: Medical Specialties, Inc., Charlotte, NC (US)

(72) Inventor: Eric Lee Gaylord, Matthews, NC (US)

(73) Assignee: Medical Specialties, Inc., Charlotte, NC (US)

( * ) Notice: Subject to any disclaimer, the term of this patent is extended or adjusted under 35 U.S.C. 154(b) by 738 days.

(21) Appl. No.: 15/355,463

(22) Filed: Nov. 18, 2016

(65) Prior Publication Data

US 2017/0143530 A1     May 25, 2017

Related U.S. Application Data

(60) Provisional application No. 62/257,933, filed on Nov. 20, 2015, provisional application No. 62/400,343, filed on Sep. 27, 2016.

(51) Int. Cl.
| | | |
|---|---|---|
| *A61F 5/00* | (2006.01) |
| *A61F 5/058* | (2006.01) |
| *A61F 5/01* | (2006.01) |

(52) U.S. Cl.
CPC ........ *A61F 5/05866* (2013.01); *A61F 5/0118* (2013.01)

(58) Field of Classification Search
CPC ...... A41D 13/00; A41D 13/08; A41D 13/087; A41D 13/088; A61F 5/00; A61F 5/01; A61F 5/0102; A61F 5/0104; A61F 5/013; A61F 5/04; A61F 5/042; A61F 5/37; A61F 5/3723; A61F 5/05; A61F 5/058; A61F 5/05841; A61F 5/05858; A61F 5/05866; A61F 5/05875; A61F 5/0118
USPC ......................................................... 602/21
See application file for complete search history.

(56) References Cited

U.S. PATENT DOCUMENTS

| | | | |
|---|---|---|---|
| 1,471,948 A | 10/1923 | Cox et al. |
| 2,206,404 A | 7/1940 | Jones |
| 4,047,250 A | 9/1977 | Norman |
| 4,081,916 A | 4/1978 | Salisbury |
| 4,190,906 A | 3/1980 | Patton, Jr. |
| 4,407,499 A | 10/1983 | Newton |
| 4,716,892 A | 1/1988 | Brunswick |
| 4,854,309 A | 8/1989 | Elsey |
| 4,881,533 A | 11/1989 | Teurlings |

(Continued)

FOREIGN PATENT DOCUMENTS

| | | |
|---|---|---|
| AU | 2008317265 A1 | 4/2009 |
| CA | 2185486 A1 | 1/1998 |

(Continued)

OTHER PUBLICATIONS

Medical Specialties, Inc., Med Spec Product Catalog, p. 7 (wrist support) and p. 12 (thumb support) (2012), four pages total.

(Continued)

*Primary Examiner* — Kim M Lewis

(74) *Attorney, Agent, or Firm* — Additon, Pendleton & Witherspoon, P.A.

(57) ABSTRACT

The present wrist brace includes an advantageous lacing configuration that provides a cast-like compression on a patient's forearm, wrist, and hand. Pulling the lacing mechanism equilibrates lace tension along the length of the wrist brace in a way that applies consistent compression to the patient's forearm and wrist.

23 Claims, 12 Drawing Sheets

(56) References Cited

U.S. PATENT DOCUMENTS

| | | |
|---|---|---|
| 5,014,689 A | 5/1991 | Meunchen et al. |
| 5,027,482 A | 7/1991 | Torppey |
| 5,058,576 A | 10/1991 | Grim et al. |
| 5,160,314 A | 11/1992 | Peters |
| 5,267,943 A | 12/1993 | Dancyger |
| 5,353,483 A | 10/1994 | Louviere |
| 5,357,691 A | 10/1994 | Hyde et al. |
| 5,415,624 A | 5/1995 | Williams |
| 5,513,657 A | 5/1996 | Nelson |
| 5,649,900 A | 7/1997 | Kline |
| 5,722,940 A | 3/1998 | Gaylord, Jr. et al. |
| 5,728,059 A | 3/1998 | Wiesmann et al. |
| 5,759,166 A | 6/1998 | Nelson et al. |
| 5,769,804 A | 6/1998 | Harris et al. |
| 5,772,620 A | 6/1998 | Szlema et al. |
| 5,928,172 A | 7/1999 | Gaylord |
| 5,982,285 A | 11/1999 | Bueche et al. |
| 6,013,045 A | 1/2000 | Gaylord |
| 6,024,715 A | 2/2000 | Maxwell |
| 6,102,880 A | 8/2000 | Nelson et al. |
| 6,228,045 B1 | 5/2001 | Gaylord et al. |
| 6,261,253 B1 | 7/2001 | Katzin |
| 6,379,321 B2 | 4/2002 | Gaylord et al. |
| 6,398,748 B1 | 6/2002 | Wilson |
| 6,540,705 B2 | 4/2003 | Norstrem et al. |
| 6,561,994 B1 | 5/2003 | Mills et al. |
| D477,409 S | 7/2003 | Mills et al. |
| 6,652,474 B1 | 11/2003 | Quinn et al. |
| 6,659,971 B2 | 12/2003 | Gaylord |
| 6,730,053 B1 | 5/2004 | Bodenschatz et al. |
| 6,852,088 B2 | 2/2005 | Gaylord |
| 6,893,410 B1 | 5/2005 | Hely |
| 6,913,582 B2 | 7/2005 | Chen et al. |
| 6,953,441 B2 | 10/2005 | Goumas |
| 6,960,176 B1 | 11/2005 | Hely et al. |
| 7,004,919 B2 | 2/2006 | Gaylord et al. |
| 7,033,331 B1 | 4/2006 | Hely |
| 7,056,298 B1 | 6/2006 | Weber |
| 7,175,603 B2 | 2/2007 | Fritsch et al. |
| 7,264,605 B2 | 9/2007 | Gaylord |
| 7,276,039 B2 | 10/2007 | Garelick et al. |
| 7,278,980 B1 | 10/2007 | Garelick et al. |
| 7,318,812 B2 | 1/2008 | Taylor et al. |
| 7,364,556 B2 | 4/2008 | Weaver, II |
| 7,402,149 B1 | 7/2008 | Garelick et al. |
| 7,651,472 B2 | 1/2010 | Gaylord et al. |
| 8,147,438 B2 | 4/2012 | Livolsi et al. |
| 8,246,560 B2 | 8/2012 | Gaylord et al. |
| 8,721,578 B2 | 5/2014 | Gaylord |
| 8,808,215 B2 | 8/2014 | Gaylord |
| 9,375,339 B2 | 6/2016 | Gaylord |
| 9,526,300 B2 | 12/2016 | Krengel |
| 9,737,430 B2 | 8/2017 | Gaylord |
| 10,045,876 B2 | 8/2018 | Kilbey |
| 10,383,404 B2 | 8/2019 | Gaylord |
| 2002/0002348 A1 | 1/2002 | Wiggins et al. |
| 2003/0041476 A1 | 3/2003 | Liu |
| 2003/0187378 A1 | 10/2003 | Gaylord et al. |
| 2004/0049141 A1 | 3/2004 | Slautterback et al. |
| 2004/0078999 A1 | 4/2004 | Freed |
| 2004/0186403 A1 | 9/2004 | Bodenschatz et al. |
| 2005/0101898 A1 | 5/2005 | Cohen |
| 2005/0197609 A1 | 9/2005 | Mills |
| 2005/0288615 A1 | 12/2005 | Gaylord |
| 2006/0149180 A1 | 7/2006 | Phelen |
| 2006/0276735 A1 | 12/2006 | Phelen et al. |
| 2007/0225630 A1 | 9/2007 | Wyatt et al. |
| 2007/0239093 A1 | 10/2007 | Wyatt et al. |
| 2008/0119771 A1 | 5/2008 | Jaccard |
| 2008/0208094 A1 | 8/2008 | Gaylord |
| 2008/0287848 A1 | 11/2008 | Jaccard |
| 2010/0298750 A1 | 11/2010 | Chiang et al. |
| 2012/0010547 A1* | 1/2012 | Hinds ............... A61F 5/0118 602/21 |
| 2012/0220910 A1 | 8/2012 | Gaylord et al. |
| 2013/0012855 A1 | 1/2013 | Giza et al. |
| 2014/0249460 A1 | 9/2014 | Gaylord |
| 2014/0330188 A1 | 11/2014 | Kilbey |
| 2014/0330190 A1* | 11/2014 | Kilbey ............... A61F 5/05866 602/21 |
| 2016/0262498 A1 | 9/2016 | Gaylord |
| 2016/0270482 A1 | 9/2016 | Krengel |
| 2017/0143526 A1 | 5/2017 | Gaylord |
| 2017/0143530 A1 | 5/2017 | Gaylord |
| 2018/0140451 A1 | 5/2018 | Gaylord |
| 2019/0015234 A1 | 1/2019 | Gaylord |

FOREIGN PATENT DOCUMENTS

| | | |
|---|---|---|
| CA | 2423778 A1 | 9/2003 |
| CA | 2703266 A1 | 4/2009 |
| WO | 2009/055080 A1 | 4/2009 |

OTHER PUBLICATIONS

Ezy Wrap, Web page for SideWinder Wrist Support, 8", MP Flex, Sep. 26, 2013, downloaded from: https://web.archive.org/web/20130926163802/http://www.ezywrap.com/p-1141-sidewinder-wrist-support-8-mp-flex.aspx, pp. 1-2.

Ezy Wrap, Product information for Sidewinder Wrist Support, 8", downloaded on Jan. 22, 2020, from: https://www.ezywrap.com/products/319-sidewindert-wrist-support-8, pp. 1-5.

Ezy Wrap, Web page for SideWinder Wrist and Forearm Support, 10.5", May 15, 2014, downloaded from: https://web.archive.org/web/20140515085202/http://www.ezywrap.com/p-1143-sidewinder-wrist-and-forearm-support-105.aspx, pp. 1-2.

Ezy Wrap, Web page for SideWinder Wrist and Forearm Support, 10.5", MP Flex, downloaded on Jan. 22, 2020, from: www.ezywrap.com/products/354-sidewindert-wrist-and-forearm-support-105-mp-flex, pp. 1-2.

Ezy Wrap, Web page for Talon Lacer Wrist Support, 8", Sep. 26, 2013, downloaded from: https://web.archive.org/web/20130926220001/http://www.ezywrap.com/p-1082-talon-lacer-wrist-support-8.aspx, pp. 1-2.

Ezy Wrap, Web page for Talon Lacer Wrist Support, 8", downloaded on Jan. 22, 2020, from: https://www.ezywrap.com/products/318-talont-lacer-wrist-support-8, pp. 1-5.

Ezy Wrap, Web page for Talon Lacer Wrist and Forearm Support, 10.5", MP Flex, Sep. 26, 2013, downloaded from: https://web.archive.org/web/20130926194856/http://www.ezywrap.com/p-1140-talon-lacer-wrist-and-forearm-support-105.aspx, pp. 1-2.

Ezy Wrap, Web page for Talon Lacer Wrist and Forearm Support, 10.5", MP Flex, downloaded on Jan. 22, 2020, from: https://www.ezywrap.com/products/351-talont-lacer-wrist-and-forearm-support-105-mp-flex, pp. 1-2.

Ezy Wrap, Web page for Ultimate Lacer Wrist and Forearm Support with Thumb Spica, 10.5", Sep. 26, 2013, Downloaded from: https://web.archive.org/web/20130926220009/http://www.ezywrap.com/p-1129-ultimate-lacer-wrist-and-foream-support-wthumb-spica-105.aspx, pp. 1-2.

Ezy Wrap, Web page for Ultimate Lacer Wrist and Foream Support, 10.5", downloaded on Jan. 24, 2020, from: https://www.ezywrap.com/products/342-ultimatet-lacer-wrist-and-foream-support-with-thumb-spica-105, pp. 1-2.

\* cited by examiner

WRIST BRACE WITH ENHANCED LACING

CROSS-REFERENCE TO PRIORITY APPLICATIONS

This application hereby claims the benefit of U.S. Patent Application No. 62/257,933 for a Wrist Brace with Enhanced Lacing (filed Nov. 20, 2015) and U.S. Patent Application No. 62/400,343 for a Wrist Brace with Enhanced Lacing (filed Sep. 27, 2016), each of which is hereby incorporated by reference in its entirety.

FIELD OF THE INVENTION

The present invention relates to a wrist brace for immobilizing and protecting a patient's forearm, wrist, and hand.

BACKGROUND

Immobilizing a patient's forearm, wrist, and hand can promote healing of bone fractures and soft-tissue injuries (e.g., sprains), and so wrist braces and supports are often used for this purpose. Conventional wrist braces are designed to fit the typical patient with somewhat frustoconical forearms, whereby the arm tapers from the elbow to the wrist (i.e., narrower near the wrist and wider near the elbow). For patients with arm shapes that deviate from standard—especially obese patients or patients with muscular forearms—conventional wrist braces can provide a poor fit. If a patient with non-standard forearms tries to manipulate a conventional wrist brace to apply uniform pressure to the patient's forearm and wrist, straps for securing the wrist brace can wrap helically along—rather than circumferentially around—the patient's forearm, rendering ineffective the mechanism for securing the wrist brace to the patient. For example, hook-and-loop fasteners can become misaligned and thus ineffectual.

SUMMARY

The present wrist brace includes an advantageous lacing configuration that provides a cast-like compression on a patient's forearm, wrist, and hand to restrict flexion, extension, and lateral movement of the wrist joint. By pulling an improved lacing mechanism, tension in a lace equilibrates along the length of the wrist brace in a way that applies consistent compression to the patient's forearm and wrist.

Exemplary wrist braces (e.g., wrist-brace splints) include a support sleeve (e.g., a U-shaped support sleeve) and a connecting panel (e.g., a stretchable radius panel or a stretchable ulnar panel) that together form a closed wrist-brace sleeve, which is securely positioned around a patient's forearm. A tensioning strap, which extends from the support sleeve, is positioned between a patient's thumb and forefinger and is releasably secured to the closed wrist-brace sleeve. A lace is threaded through openings (e.g., eyelets) or other lace-redirection mechanisms positioned along the edges of the support sleeve and on a lacing closure tab. Regardless of the shape and girth of the patient's forearm, pulling the lacing closure tab circumferentially around the closed wrist-brace sleeve and thereupon releasably securing the lacing closure tab to the closed wrist-brace sleeve achieves a cast-like compression of the wrist brace to the patient's forearm and wrist.

In an exemplary wrist-brace embodiment, the wrist brace includes a U-shaped support sleeve having a dorsal section, a palmar section, and an ulnar section positioned between the dorsal section and the palmar section. The U-shaped support sleeve may be formed from flexible, low-stretch material to help stabilize the patient's forearm, wrist, and hand. Dorsal lace-redirection mechanisms (e.g., dorsal eyelets) are positioned at or near the U-shaped support sleeve's dorsal section, and palmar lace-redirection mechanisms (e.g., palmar eyelets) are positioned at or near the U-shaped support sleeve's palmar section. A radius panel, which is typically stretchable and/or elastic, is secured to the U-shaped support sleeve's dorsal section and the U-shaped support sleeve's palmar section so that together the U-shaped support sleeve and the radius panel form a closed wrist-brace sleeve. The wrist brace further includes at least one lacing closure tab having one or more closure-tab lace-redirection mechanisms (e.g., closure-tab eyelets). A lace, which has a first end fixed to the U-shaped support sleeve nearer the U-shaped support sleeve's proximal end and a second end fixed to the U-shaped support sleeve nearer the U-shaped support sleeve's distal end, is freely threaded though the respective dorsal lace-redirection mechanisms, palmar lace-redirection mechanisms, and closure-tab lace-redirection mechanisms. This exemplary wrist-brace may include an oblique palmar-tensioning strap that extends from the distal end of the U-shaped support sleeve's palmar section. The oblique palmar-tensioning strap is positioned between a patient's thumb and forefinger and is releasably affixed to the U-shaped support sleeve when the wrist brace is secured to the patient's wrist and forearm.

In another exemplary wrist-brace embodiment, the wrist brace includes a U-shaped support sleeve having a dorsal section, a palmar section, and a radius section positioned between the dorsal section and the palmar section. The U-shaped support sleeve may be formed from flexible, low-stretch material to help stabilize the patient's forearm, wrist, and hand. Dorsal lace-redirection mechanisms (e.g., dorsal eyelets) are positioned at or near the U-shaped support sleeve's dorsal section, and palmar lace-redirection mechanisms (e.g., palmar eyelets) are positioned at or near the U-shaped support sleeve's palmar section. An ulnar panel, which is typically stretchable and/or elastic, is secured to the U-shaped support sleeve's dorsal section and the U-shaped support sleeve's palmar section so that together the U-shaped support sleeve and the ulnar panel form a closed wrist-brace sleeve. The wrist brace further includes at least one lacing closure tab having one or more closure-tab lace-redirection mechanisms (e.g., closure-tab eyelets). A lace, which has a first end fixed to the U-shaped support sleeve nearer the U-shaped support sleeve's proximal end and a second end fixed to the U-shaped support sleeve nearer the U-shaped support sleeve's distal end, is freely threaded though the respective dorsal lace-redirection mechanisms, palmar lace-redirection mechanisms, and closure-tab lace-redirection mechanisms. This exemplary wrist-brace may include a thumb-tensioning strap that extends from the distal end of the U-shaped support sleeve's radius section. The thumb-tensioning strap is positioned between a patient's thumb and forefinger, wrapped around the patient's thumb, and then securely and releasably affixed to the U-shaped support sleeve when the wrist brace is secured to the patient's wrist and forearm.

The foregoing illustrative summary, as well as other exemplary objectives and/or advantages of the invention, and the manner in which the same are accomplished, are further explained within the following detailed description and its accompanying drawings and photographs.

DETAILED DESCRIPTION

The present wrist braces with improved lacing are described herein with reference to the accompanying drawings, which depict exemplary wrist-brace embodiments that should not be construed as limiting the scope of the invention. Rather, the exemplary wrist-brace embodiments are provided so this disclosure will be thorough and complete to convey to those having ordinary skill in the art the scope of the invention. In the accompanying drawings, like numbers refer to like elements.

As described herein, the terms "interior surface" and "inner surface" refer to a planar side closest to the patient's hand, and the terms "exterior surface" and "outer surface" refer to a planar side farthest from the patient's hand (i.e., an outer surface is opposite an inner surface).

The term "section" refers in context to a portion or an area of the wrist-brace sleeve. The term "dorsal" refers to the topside of the wrist brace or hand. The term "palmar" refers to the underside of the wrist brace or hand (i.e., the palm). The term "radius" refers to the inner side of the wrist brace, hand, and/or wrist (i.e., the thumb side of the forearm). The term "ulnar" refers to the outer side of the wrist brace, hand, and/or wrist (i.e., the side of the forearm opposite the thumb). The term "proximal" refers to the part of the wrist brace or hand that is closer to the patient's elbow, and the term "distal" refers to the part of the wrist brace or hand farther from the patient's elbow.

The terms "positioned" or "positioning" are used conventionally to embrace one element being fixed or releasably secured to another element. For example, a first element may be positioned against a second element (or positioned between second and third elements) by sewing, by hook-and-loop fasteners, or by other known mechanisms for physically attaching physical elements to each other. The terms "fixed," "affixed," and "secured" may include sewn, made integral with, adhered with adhesive, or bonded (e.g., fused with heat).

The terms "freely threaded" and "freely interlaced" are used herein in accordance with the wrist-brace embodiments depicted in FIGS. 1-12 to refer to a lace that is moveably connected to a lace-redirection mechanism, such as an eyelet, rather than fixedly attached to a lace-redirection mechanism. For example, as described herein, a lace that is "freely threaded" through a closure-tab lace-redirection mechanism, which is positioned on or otherwise formed through a lacing closure tab, can facilitate movement of the lacing closure tab along the lace.

Figure 5:
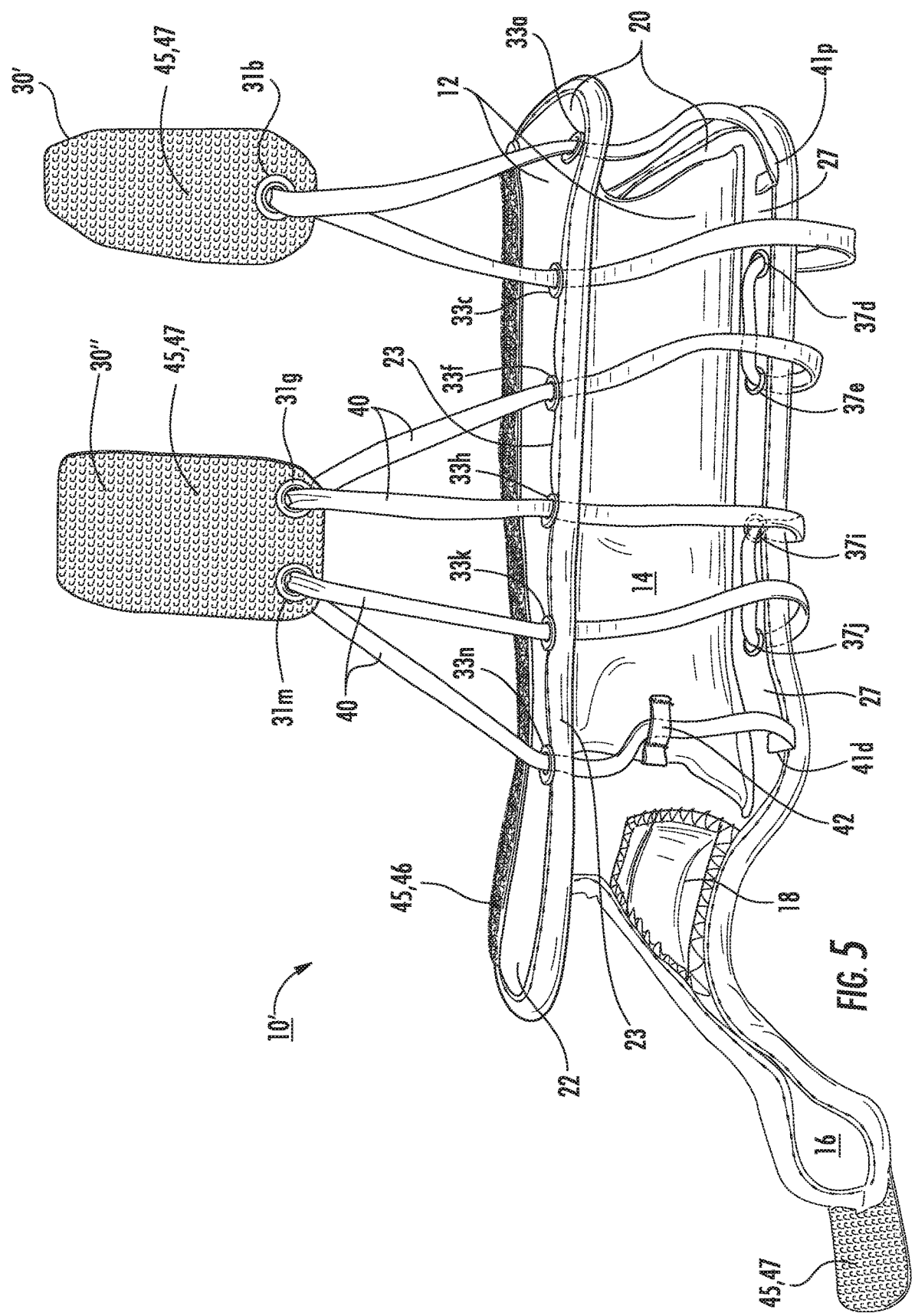
FIGS. 5-6 are perspective views of another exemplary wrist-brace embodiment having an advantageous lacing configuration.
Figure 6:
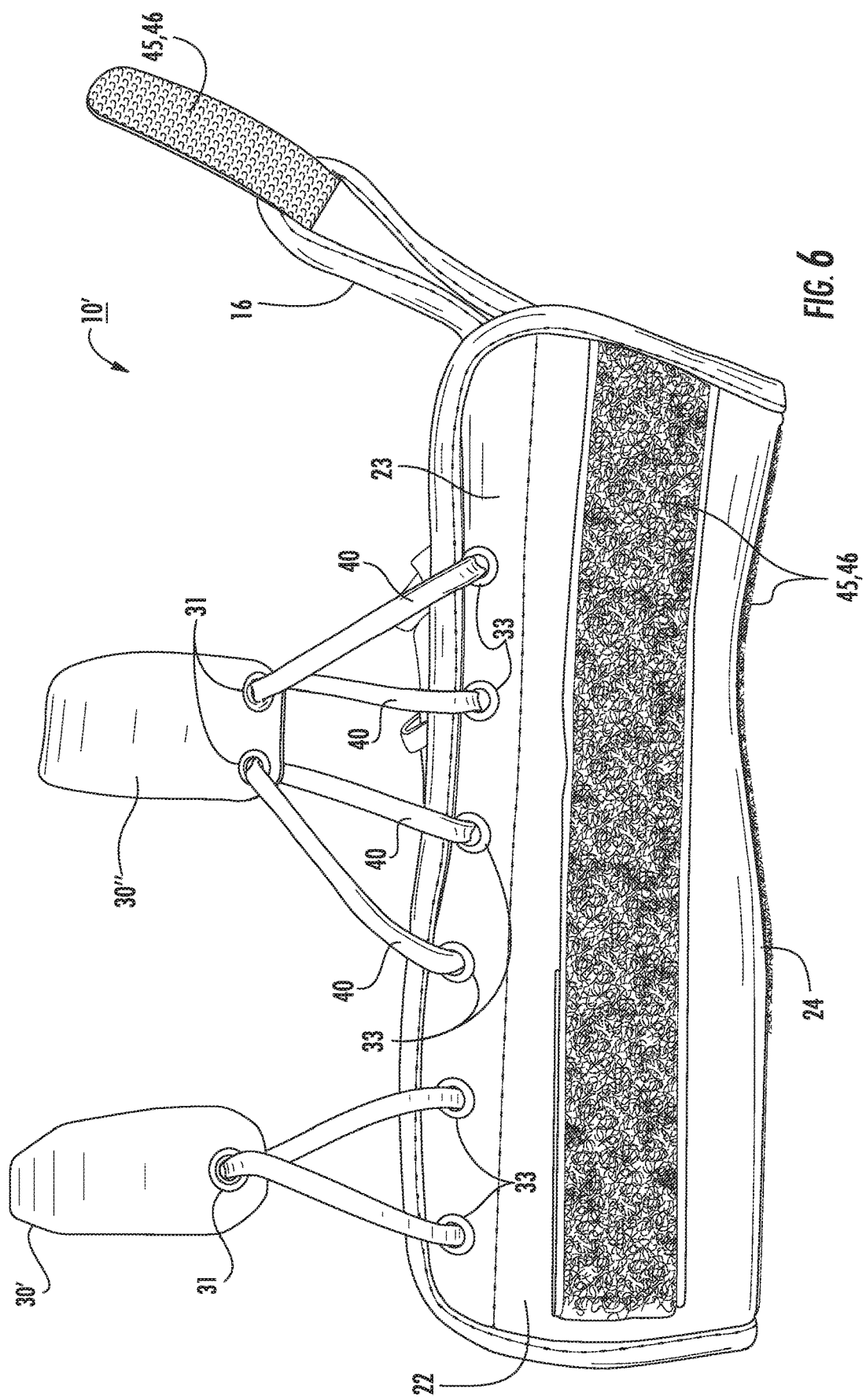

FIGS. 1-4 depict an exemplary wrist-brace embodiment sized for a patient. FIGS. 5-6 depict a similar, but longer, exemplary wrist-brace embodiment sized for a patient. Each wrist brace is configured for either a left forearm, wrist, and hand or a right forearm, wrist, and hand. Those having ordinary skill in the art will understand that a left-hand orientation is a mirror image of a right-hand orientation. FIGS. 1-6 illustrate a right-hand orientation. Appendix I includes photographs of an exemplary prototype of the wrist brace depicted in FIGS. 1-4, and Appendix II includes photographs of an exemplary prototype of the longer wrist brace depicted in FIGS. 5-6. The description of the shorter wrist-brace embodiment depicted in FIGS. 1-4 typically applies to the longer wrist-brace embodiment depicted in FIGS. 5-6, except as noted in the supporting description, figures, and photographs.

With reference to the exemplary wrist brace 10 depicted in FIGS. 1-4 (and, as noted, the related, longer exemplary wrist brace 10' depicted in FIGS. 5-6), the wrist brace 10 includes a closed wrist-brace sleeve 12 defining an interior surface and an exterior surface. The closed wrist-brace sleeve 12 is formed by a stretchable radius panel 14 connected to a U-shaped support sleeve 20, which might also be considered a C-shaped support sleeve.

The U-shaped support sleeve 20 includes a topside dorsal section 22, an ulnar section 24, and an underside palmar section 26. The ulnar section 24 is contiguously positioned between the dorsal section 22 and the palmar section 26 to define the U-shaped support sleeve 20. The topside dorsal section 22 is positioned opposite the underside palmar section 26, and the ulnar section 24 is positioned opposite the stretchable radius panel 14. Typically, the U-shaped support sleeve 20, which opens to a patient's forearm radius, is substantially inelastic (e.g., formed from flexible, low-stretch material) to help stabilize the patient's wrist and hand.

As used herein, the term "elastic" generally refers to material that can be readily stretched or expanded, and then can return to its initial shape (i.e., elastic materials resist deformation by stretching), and the term "inelastic" generally refers to material that resists stretching and elongation. The U-shaped support sleeve 20 may be constructed of lightweight suede-like polymeric materials or other lightweight fabrics (e.g., nylon or PVC) having excellent strength and durability. The interior surface of the U-shaped support sleeve 20 may be enhanced with nonwoven polymeric materials (e.g., nonwoven polyolefins), such as felt fabric, to provide cushioning and support.

The stretchable radius panel 14, which may be cushioned for the patient's comfort, is affixed to both the U-shaped support sleeve's dorsal section 22 and the U-shaped support sleeve's palmar section 26, thereby closing the gap in the U-shaped support sleeve 20 to form the closed wrist-brace sleeve 12. In addition, the stretchable radius panel 14 is typically positioned within the gap in the U-shaped support sleeve 20 to define both an outer dorsal strip 23 and an outer palmar strip 27. More specifically, the outer dorsal strip 23 is defined by the stretchable radius panel 14 and an adjacent outer edge of the U-shaped support sleeve 20, and the outer palmar strip 27 is defined by the stretchable radius panel 14 and an adjacent outer edge of the U-shaped support sleeve 20.

An oblique palmar-tensioning strap 16 extends from the distal end of the U-shaped support sleeve's palmar section 26. The oblique palmar-tensioning strap 16 is positioned between the patient's thumb and forefinger (i.e., near the thenar space) and then securely and releasably affixed to the U-shaped support sleeve's dorsal section 22 (e.g., via hook-and-loop fasteners, such as VELCRO-brand fasteners). The oblique palmar-tensioning strap 16 helps to position and secure the wrist brace 10 to the patient's wrist and forearm.

An optional palmar pad 18, which is positioned at the transition between the U-shaped support sleeve's palmar section 26 and the oblique palmar-tensioning strap 16, provides the patient with enhanced comfort and support.

Figure 1:
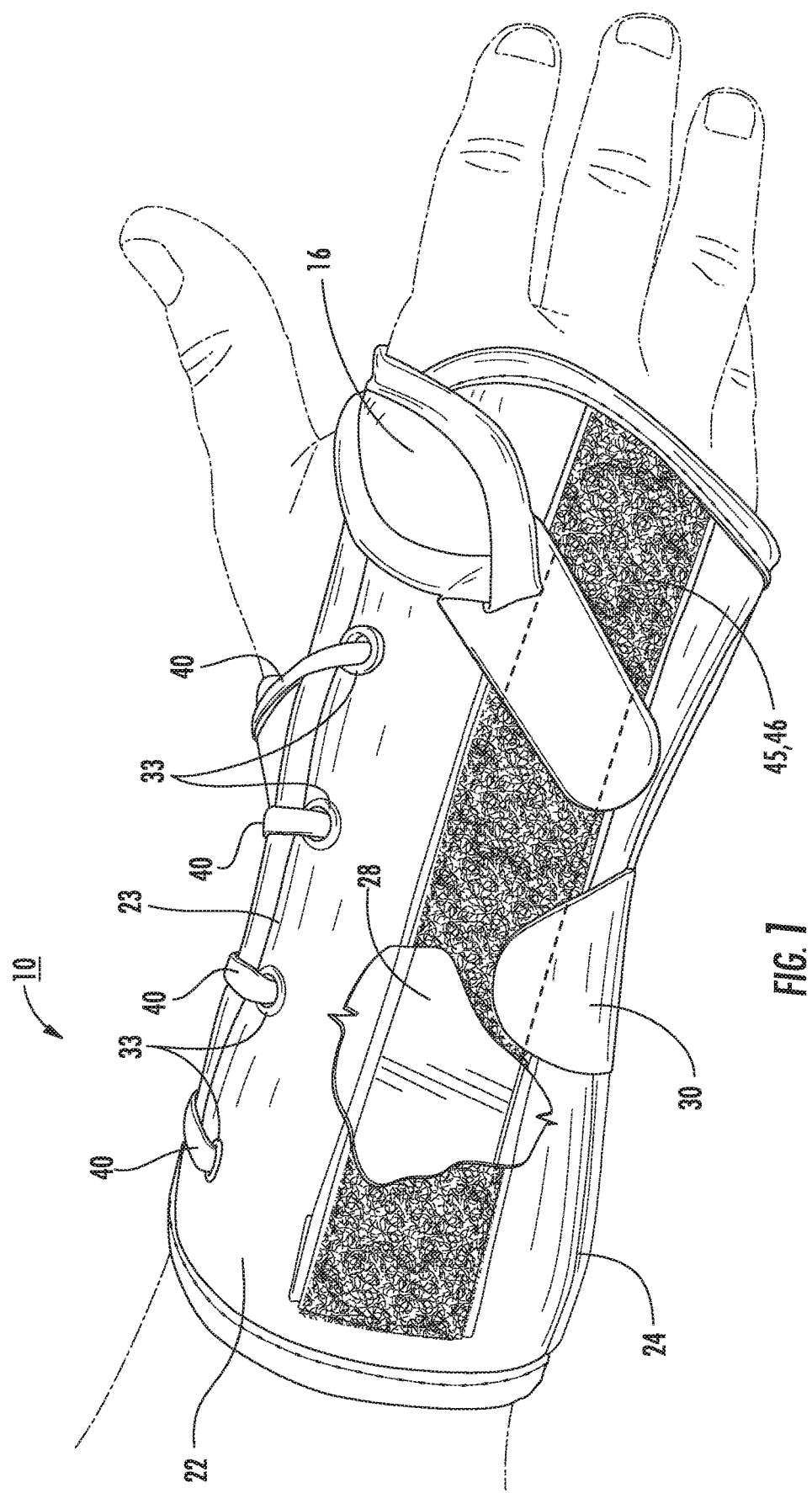
FIGS. 1-4 are perspective views of an exemplary wrist-brace embodiment having an advantageous lacing configuration.
Figure 2:
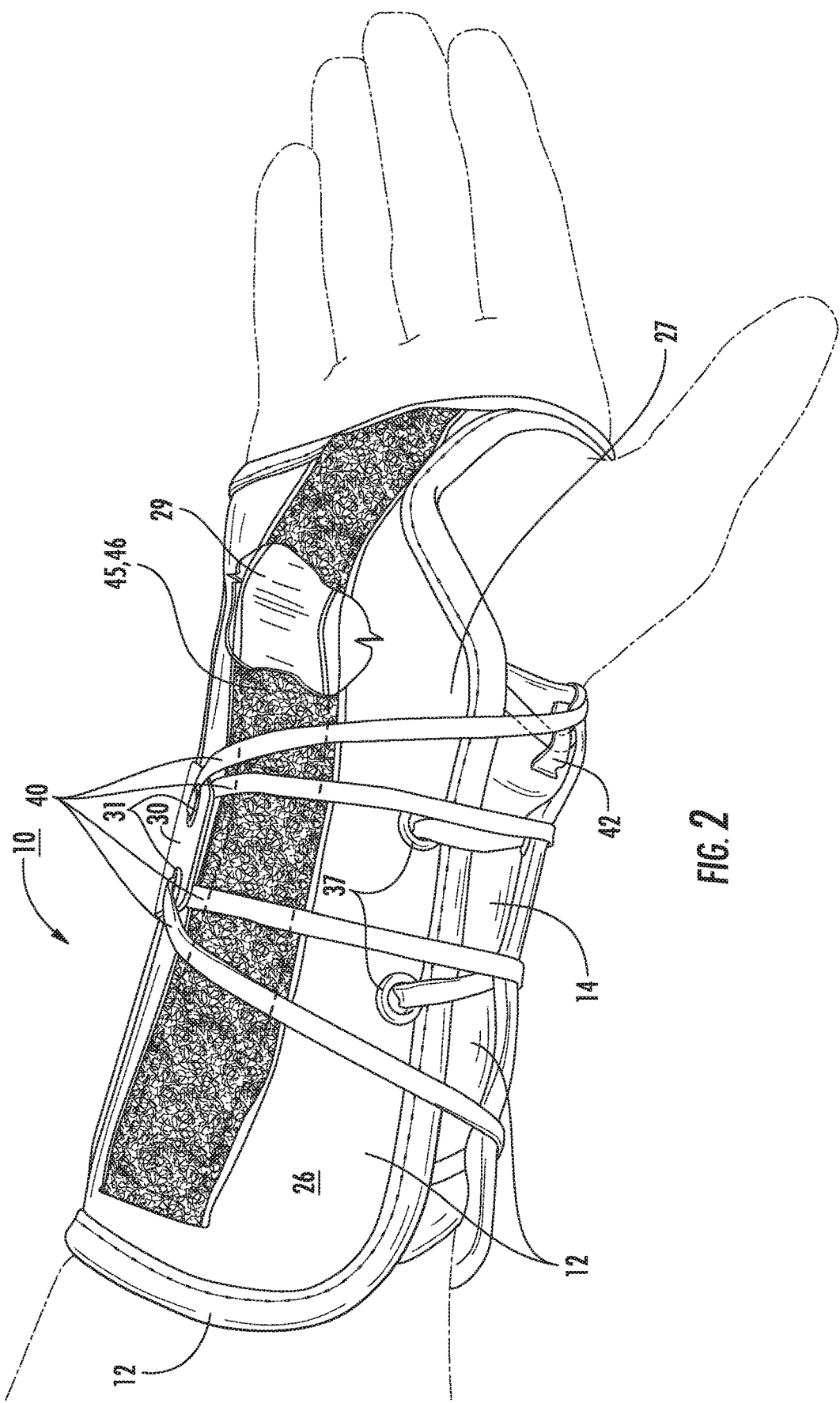
Figure 3:
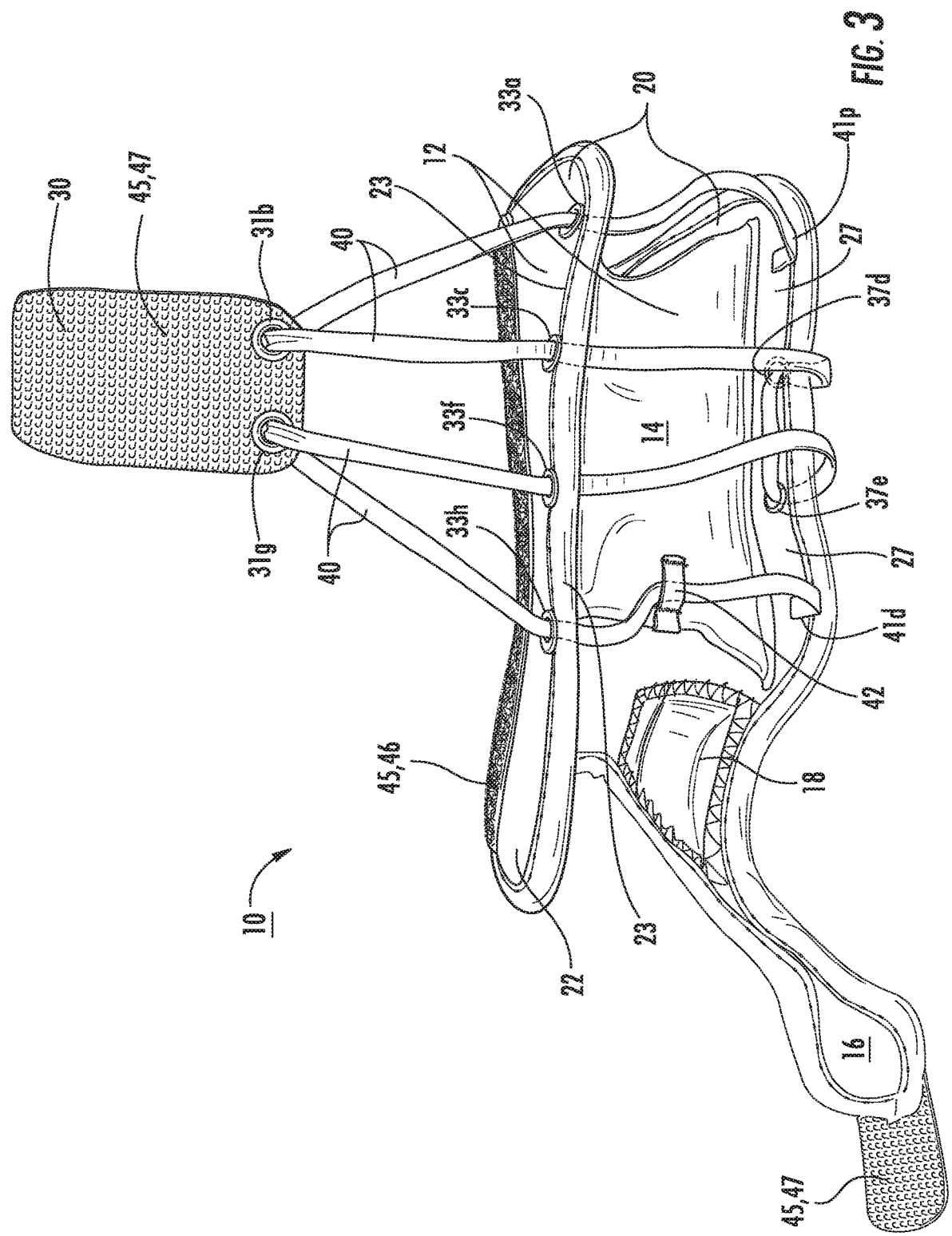
Figure 4:
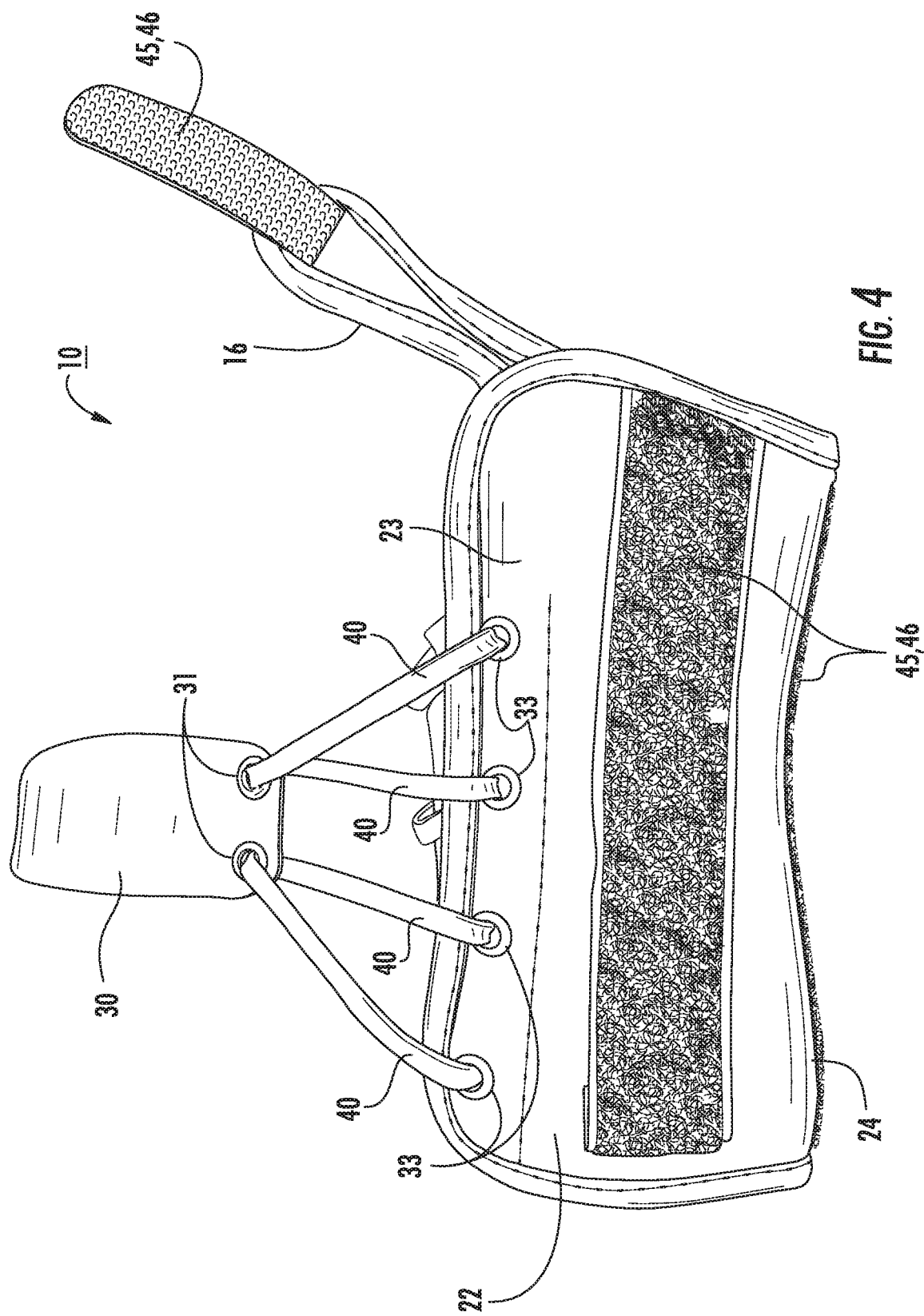

The U-shaped support sleeve 20 can include stabilizing members to limit flexion and extension. In the exemplary wrist-brace embodiments depicted in FIGS. 1-4 and FIGS. 5-6, a longitudinal stiffening dorsal stay 28 is internally secured within the U-shaped support sleeve's dorsal section 22, and a longitudinal stiffening palmar stay 29 is internally secured within the U-shaped support sleeve's palmar section 26. As shown in FIGS. 2-3, the palmar stay 29 conforms to the shape of the patient's forearm, wrist, and palm. In addition, a longitudinal ulnar stay (not shown) can be internally secured within the U-shaped support sleeve's ulnar section 24. Including stays on two or more sides of the wrist brace (e.g., a wrist brace having a dorsal stay, a palmar stay, and an ulnar stay) protects against impact forces and helps reduce the likelihood of reinjuring the patient's wrist and hand.

The stabilizing members (i.e., stays) may be formed from metals, alloys, plastics, or other materials providing sufficient rigidity to resist movement and retain a desired shape while maintaining adequate adjustability for wear on the forearm, wrist, and hand. Typically, the stabilizing members are made of aluminum. In some embodiments, the stabilizing members can be manually adjusted to conform to the shape of the patient's forearm, wrist, and/or palm. Adjustable stabilizing members are sufficiently rigid to resist movement of the U-shaped support sleeve's distal end relative to the U-shaped support sleeve's proximal end and are sufficiently strong to provide protection against forces acting against the wrist brace (e.g., impact forces). The stabilizing members (i.e., stays) may be permanently secured within the wrist brace (e.g., an internally secured, permanent stay) or may be positioned within pockets formed in the U-shaped support sleeve to facilitate placement and removal of the stays (e.g., an internally secured, removable stay). Alternatively, the stabilizing members might be externally secured to the U-shaped support sleeve.

Dorsal eyelets 33 (or similar openings, such as reinforced holes and/or slots, or other dorsal lace-redirection mechanisms, such as loops, hooks, folded webbing, and/or buckles) are formed through or otherwise positioned at or near (e.g., positioned upon) the U-shaped support sleeve's dorsal section 22 (e.g., at the outer dorsal strip 23). Similarly, palmar eyelets 37 (or similar openings, such as reinforced holes and/or slots, or other palmar lace-redirection mechanisms, such as loops, hooks, folded webbing, and/or buckles) are formed through or otherwise positioned at or near (e.g., positioned upon) the U-shaped support sleeve's palmar section 26 (e.g., at the outer palmar strip 27). The shorter exemplary wrist brace 10 depicted in FIGS. 1-4 includes four dorsal eyelets 33*a*, 33*c*, 33*f*, 33*h* and two palmar eyelets 37*d*, 37*e* (i.e., imbalanced eyelets on either side of the U-shaped support sleeve 20). The longer exemplary wrist brace 10' depicted in FIGS. 5-6 includes six dorsal eyelets 33*a*, 33*c*, 33*f*, 33*h*, 33*k*, 33*n* and four palmar eyelets 37*d*, 37*e*, 37*i*, 37*j* (i.e., imbalanced eyelets on either side of the U-shaped support sleeve 20). Those having ordinary skill in the art will understand that exemplary wrist braces according to the present invention may employ any lace-redirection mechanisms (e.g., reinforced openings, or external loops, hooks, folded webbing, and/or buckles) in addition to or instead of eyelets.

Moreover, it is within the scope of the present wrist-brace invention to include one or more external flaps (not shown) on the exterior of the U-shaped support sleeve to facilitate redirection of a lace. In one wrist-brace embodiment, a dorsal flap having eyelets or other lace-redirection mechanisms can be positioned upon the U-shaped support sleeve's dorsal section (e.g., near the stretchable radius panel), and the lace may be guided through the dorsal flap's lace-redirection mechanisms (e.g., eyelets) and the palmar eyelets (or other lace-redirection mechanisms) to promote even closure of the closed wrist-brace sleeve and to achieve cast-like compression on a patient's forearm, wrist, and hand. In another wrist-brace embodiment, a palmar flap having eyelets or other lace-redirection mechanisms can be positioned upon the U-shaped support sleeve's palmar section (e.g., near the stretchable radius panel), and the lace may be guided through the palmar flap's lace-redirection mechanisms (e.g., eyelets) and the dorsal eyelets (or other lace-redirection mechanisms) to promote even closure of the closed wrist-brace sleeve and to achieve cast-like compression on a patient's forearm, wrist, and hand. In yet another wrist-brace embodiment, a lace may be guided through both (i) a dorsal flap having eyelets or other lace-redirection mechanisms and (ii) a palmar flap having eyelets or other lace-redirection mechanisms to achieve cast-like compression on a patient's forearm, wrist, and hand, thereby restricting flexion, extension, and lateral movement of the wrist joint.

The shorter exemplary wrist brace 10 depicted in FIGS. 1-4 includes a lacing closure tab 30 through which one or more closure-tab eyelets 31 are formed. The longer exemplary wrist brace 10' depicted in FIGS. 5-6 includes multiple lacing closure tabs 30' and 30" through which one or more closure-tab eyelets 31 are formed. More generally, closure-tab eyelets 31 (or similar openings, such as reinforced holes and/or slots, or other closure-tab lace-redirection mechanisms, such as loops, hooks, folded webbing, and/or buckles) may be formed through or otherwise positioned at or near (e.g., positioned upon) the lacing closure tab(s) 30.

Each lacing closure tab 30 includes a mechanism, such as a hook-and-loop fastener, to releasably secure the lacing closure tab 30 to another part of the wrist brace 10. In the shorter exemplary wrist-brace embodiment depicted in FIG. 3, two closure-tab eyelets 31*b*, 31*g* are formed through or otherwise positioned upon the lacing closure tab 30. In the longer exemplary wrist-brace embodiment depicted in FIG. 5, one closure-tab eyelet 31*b* is formed through or otherwise positioned upon the proximal lacing closure tab 30' and two closure-tab eyelets 31*g*, 31*m* are formed through or otherwise positioned upon the distal lacing closure tab 30". The closure-tab eyelets 31 help to ensure that each lacing closure tab 30 remains centered on the U-shaped support sleeve 20 as the lacing closure tab 30 is pulled over and around the closed wrist-brace sleeve 12.

A lace 40 is freely threaded (or otherwise interlaced) though the respective dorsal eyelets 33, palmar eyelets 37, and closure-tab eyelets 31. The lace 40, which typically resists excessive stretching, can move freely to accommodate the typical non-cylindrical anatomy of a patient's forearm in which the arm tapers from the elbow to the wrist (e.g., a frustoconical shape). This free movement of the lace 40 facilitates consistent tension along the lace 40. This even tension is transferred to the respective dorsal eyelets 33, palmar eyelets 37, and closure-tab eyelets 31 through which the lace 40 is interlaced.

Each lacing closure tab 30 is moveably connected to the lace 40. When the lacing closure tab 30 is not releasably secured to another part of the wrist brace (e.g., releasably affixed to the closed wrist-brace sleeve 12), the lacing closure tab 30 can move substantially freely along the lace 40. The shorter exemplary wrist brace 10 depicted in FIGS. 1-4 does not fixedly attach the one lace 40 to the lacing closure tab 30, either fully or partially. Similarly, the longer exemplary wrist brace 10' depicted in FIGS. 5-6 does not fixedly attach the one lace 40 to the respective closure tabs 30' and 30", either fully or partially. Rather, in these exemplary wrist-brace embodiments, the lace 40 may pass substantially freely through each of the closure-tab eyelets 31. As depicted in FIGS. 1-6, each strand of lace 40 from a dorsal eyelet 33 to a closure tab 30 is freely threaded through a closure-tab eyelet 31. This "free-floating" closure-tab design enables the patient to readily equilibrate lace tension through the various eyelets (i.e., the dorsal eyelets 33 and palmar eyelets 37) positioned along the length of the wrist brace in a way that applies substantially consistent compression to the patient's forearm and wrist. The lace 40 and each moveably attached lacing closure tab 30 wrap circumferentially around—rather than helically along—the patient's forearm in a way that uniformly closes and tensions the closed wrist-brace sleeve 12.

Typically, one lace 40 has (i) a first end fixed to the U-shaped support sleeve's interior surface at the U-shaped support sleeve's proximal end (e.g., secured at either the proximal end of the outer palmar strip 27 or the proximal end of the outer dorsal strip 23) and (ii) a second end fixed to the U-shaped support sleeve's interior surface at the U-shaped support sleeve's distal end (e.g., secured at either the distal end of the outer palmar strip 27 or the distal end of the outer dorsal strip 23). In this embodiment, either the dorsal eyelets 33 or the palmar eyelets 37 are positioned between the lace's first fixed end and the lace's second fixed end.

As illustrated in FIGS. 1-4 in which the ends of lace 40 are fixed to the outer palmar strip 27, pulling the lacing closure tab 30 away from the U-shaped support sleeve's dorsal section 22 (and over and around the U-shaped support sleeve's palmar section 26) uniformly closes and tensions the closed wrist-brace sleeve 12 by drawing together the U-shaped support sleeve's dorsal section 22 and the U-shaped support sleeve's palmar section 26. Similarly, in an alternative wrist-brace embodiment (not shown) in which the ends of lace 40 are fixed to the outer dorsal strip 27, pulling the lacing closure tab away from the U-shaped support sleeve's palmar section 26 (and over and around the U-shaped support sleeve's dorsal section 22) uniformly closes and tensions the closed wrist-brace sleeve 12 by drawing together the U-shaped support sleeve's palmar section 26 and the U-shaped support sleeve's dorsal section 22. These same considerations apply to wrist-brace embodiments that include multiple lacing closure tabs, such as the proximal lacing closure tab 30' and the distal lacing closure tab 30" illustrated in FIGS. 5-6.

In the shorter exemplary wrist-brace embodiment depicted in FIG. 3, a single lace 40 has (i) a first proximal end fixed to the U-shaped support sleeve's interior surface nearer the U-shaped support sleeve's proximal end (i.e., a proximal fixation 41p toward the proximal end of the outer palmar strip 27) and (ii) a second distal end fixed to the U-shaped support sleeve's interior surface nearer the U-shaped support sleeve's distal end (i.e., a distal fixation 41d toward the distal end of the outer palmar strip 27). In the exemplary wrist-brace embodiment depicted in FIG. 3, two palmar eyelets 37d, 37e are formed along outer palmar strip 27 between the lace's proximal fixation 41p and the lace's distal fixation 41d, and four dorsal eyelets 33a, 33c, 33f, 37h are formed along the outer dorsal strip 23.

As illustrated in the exemplary wrist-brace embodiment depicted in FIG. 3, the wrist brace 10 includes a compression-enhancing lacing configuration that readily equilibrates (e.g., simultaneously evens) the tension in the lace 40 as the lacing closure tab 30 is extended from the closed wrist-brace sleeve 12. From the proximal end of the wrist brace 10 to the distal end of the wrist brace 10, the lace 40 passes from its proximal fixation 41p to and through an outer proximal dorsal eyelet 33a, to and through a proximal closure-tab eyelet 31b, to and through an inner proximal dorsal eyelet 33c, to and through a proximal palmar eyelet 37d. The lace 40 then passes lengthwise along the interior surface of the outer palmar strip 27 from the proximal palmar eyelet 37d to and through a distal palmar eyelet 37e so that, between the proximal palmar eyelet 37d and the distal palmar eyelet 37e, the lace 40 is substantially parallel to the adjacent outer edge of the U-shaped support sleeve 20. The lace 40 then passes from the distal palmar eyelet 37e to and through an inner distal dorsal eyelet 33f, to and through a distal closure-tab eyelet 31g, to and through an outer distal dorsal eyelet 33h, and to the distal fixation 41d.

In the longer exemplary wrist-brace embodiment depicted in FIG. 5, a single lace 40 has (i) a first proximal end fixed to the U-shaped support sleeve's interior surface near the U-shaped support sleeve's proximal end (i.e., a proximal fixation 41p toward the proximal end of the outer palmar strip 27) and (ii) a second distal end fixed to the U-shaped support sleeve's interior surface nearer the U-shaped support sleeve's distal end (i.e., a distal fixation 41d toward the distal end of the outer palmar strip 27). In the exemplary wrist-brace embodiment depicted in FIG. 5, four palmar eyelets 37d, 37e, 37i, 37j are formed along outer palmar strip 27 between the lace's proximal fixation 41p and the lace's distal fixation 41d, and six dorsal eyelets 33a, 33c, 33f, 33h, 33k, 33n are formed along the outer dorsal strip 23.

As illustrated in the exemplary wrist-brace embodiment depicted in FIG. 5, the wrist brace 10' includes a compression-enhancing lacing configuration that readily equilibrates the tension in the lace 40 as the lacing closure tabs 30', 30" are extended from the closed wrist-brace sleeve 12. From the proximal end of the wrist brace 10' to the distal end of the wrist brace 10', the lace 40 passes from its proximal fixation 41p to and through an outermost proximal dorsal eyelet 33a, to and through a closure-tab eyelet 31b formed in the proximal lacing closure tab 30', to and through a central proximal dorsal eyelet 33c, to and through an outer proximal palmar eyelet 37d. The lace 40 then passes lengthwise along the interior surface of the outer palmar strip 27 from the outer proximal palmar eyelet 37d to and through an inner proximal palmar eyelet 37e so that, between the outer proximal palmar eyelet 37d and the inner proximal palmar eyelet 37e, the lace 40 is substantially parallel to the adjacent outer edge of the U-shaped support sleeve 20. The lace 40 then passes from the inner proximal palmar eyelet 37e to and through an inner proximal dorsal eyelet 33f, to and through a first distal closure-tab eyelet 31g formed in the distal lacing closure tab 30", to and through an inner distal dorsal eyelet 33h, to and through an inner distal palmar eyelet 37i. The lace 40 then passes lengthwise along the interior surface of the outer palmar strip 27 from the inner distal palmar eyelet 37i to and through an outer distal palmar eyelet 37j so that, between the inner distal palmar eyelet 37i and the outer distal palmar eyelet 37j, the lace 40 is substantially parallel to the adjacent outer edge of the U-shaped support sleeve 20. The lace 40 then passes from the outer distal palmar eyelet 37j to and through a central distal dorsal eyelet 33k, to and through a second distal closure-tab eyelet 31m formed in the distal lacing closure tab 30", to and through an outermost distal dorsal eyelet 33n, and to the distal fixation 41d.

Optionally, the lace 40 passes through one or more lacing channels 42, which may be secured to or otherwise formed in the stretchable radius panel 14. In the shorter exemplary wrist-brace embodiment depicted in FIG. 3, the lace 40 passes through one lacing channel 42 secured to the stretchable radius panel 14 as the lace 40 passes from the outer distal dorsal eyelet 33h to the distal fixation 41d. In the longer exemplary wrist-brace embodiment depicted in FIG. 5, the lace 40 passes through one lacing channel 42 secured to the stretchable radius panel 14 as the lace 40 passes from the outermost distal dorsal eyelet 33n to the distal fixation 41d. As will be appreciated by those having ordinary skill in the art, each lacing channel 42 should be positioned to facilitate passage of the lace 40 between the outer palmar strip 27 and the outer dorsal strip 23. For example, positioning lacing channel(s) 42 at either the distal end or the proximal end of the stretchable radius panel 14, or both the distal end and the proximal end of the stretchable radius panel 14, helps to maintain the proper positioning of stretchable radius panel 14 against the patient's forearm as shown in FIG. 2. In practice, securing the lace 40 to the stretchable radius panel 14 via one or more lacing channels 42, typically at the distal end and/or proximal end of a cushioned, stretchable radius panel 14, reduces patient discomfort by preventing the lace 40 from migrating beyond the end of the stretchable radius panel 14 when the wrist brace 10 is compressively and securely applied to the patient's wrist and forearm.

As illustrated in the exemplary wrist-brace embodiments depicted in FIGS. 1-4 and FIGS. 5-6, hook-and-loop fasteners 45 are secured to the surfaces of the wrist brace 10 to facilitate closure of the wrist brace 10 to the patient's forearm, wrist, and hand. For example, loop-fasteners 46 (e.g., loop-fastener strips) can be secured to the outer surfaces of the U-shaped support sleeve 20, typically at the topside dorsal section 22, the ulnar section 24, and the underside palmar section 26. Hook-fasteners 47 are provided elsewhere on the wrist brace 10, such as on a surface of each lacing closure tab 30 and a surface at the end of the oblique palmar-tensioning strap 16.

As illustrated in FIGS. 1-4 and FIGS. 5-6, the patient may secure the wrist brace 10 to his forearm, wrist, and hand by pulling a lacing closure tab 30 perpendicularly away from the U-shaped support sleeve's dorsal section 22 and over and around the U-shaped support sleeve's palmar section 26. This evenly closes and tensions the closed wrist-brace sleeve 12 by drawing together the U-shaped support sleeve's dorsal section 22 and the U-shaped support sleeve's palmar section 26. Depending on the girth of the patient's forearm, the hook-fasteners 47 on a surface of the lacing closure tab 30 will engage one or more loop-fasteners 46 positioned upon the respective outer surfaces of the dorsal section 22, the ulnar section 24, and the palmar section 26. The hook-fastener 47 at the end of the oblique palmar-tensioning strap 16 can be releasably secured to the U-shaped support sleeve's dorsal section 22.

Figure 11:
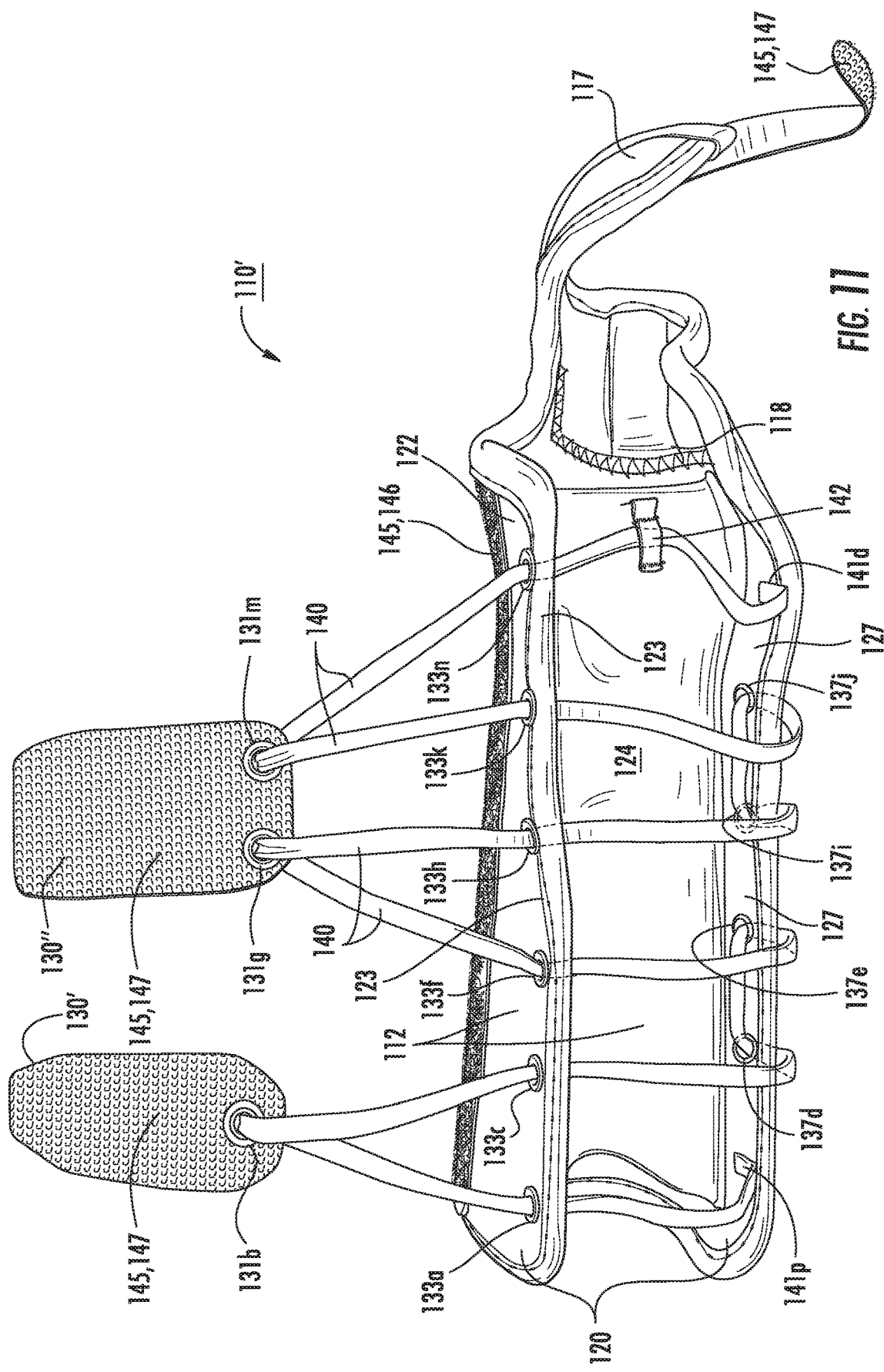
FIGS. 11-12 are perspective views of yet another exemplary wrist-brace embodiment having an advantageous lacing configuration.
Figure 12:
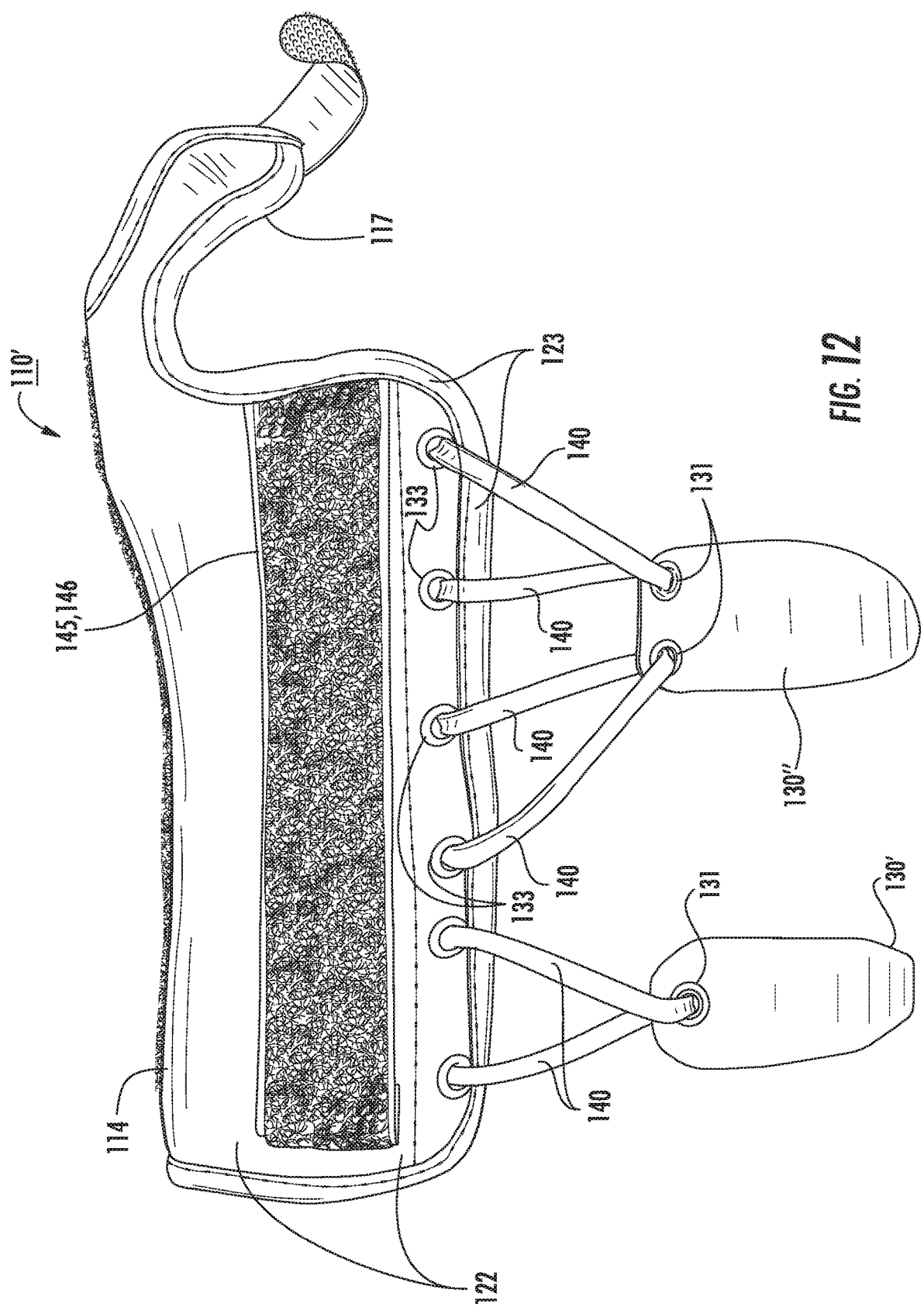

FIGS. 7-10 depict another exemplary wrist-brace embodiment sized for a patient. FIGS. 11-12 depict a similar, but longer, exemplary wrist-brace embodiment sized for a patient. Each of these wrist braces includes more substantial thumb support as compared with the wrist-brace embodiments depicted in FIGS. 1-6. As with the wrist-brace embodiments depicted in FIGS. 1-6, the wrist brace embodiments depicted in FIGS. 7-12 are configured for either a left forearm, wrist, and hand or a right forearm, wrist, and hand. Those having ordinary skill in the art will understand that a left-hand orientation is a mirror image of a right-hand orientation. FIGS. 7-12 illustrate a right-hand orientation. Appendix III includes photographs of an exemplary prototype of the wrist brace depicted in FIGS. 7-10, and Appendix IV includes photographs of an exemplary prototype of the longer wrist brace depicted in FIGS. 11-12.

The description of the shorter wrist-brace embodiment depicted in FIGS. 7-10 typically applies to the longer wrist-brace embodiment depicted in FIGS. 11-12, except as noted in the supporting description, figures, and photographs.

With reference to the exemplary wrist brace 110 depicted in FIGS. 7-10 (and, as noted, the related, longer exemplary wrist brace 110' depicted in FIGS. 11-12), the wrist brace 110 includes a closed wrist-brace sleeve 112 defining an interior surface and an exterior surface. The closed wrist-brace sleeve 112 is formed by a stretchable ulnar panel 124 connected to a U-shaped support sleeve 120.

The U-shaped support sleeve 120 includes a topside dorsal section 122, a radius section 114, and an underside palmar section 126. The radius section 114, which is designed to extend to the base of a patient's thumb, is contiguously positioned between the dorsal section 122 and the palmar section 126 to define the U-shaped support sleeve 120. The topside dorsal section 122 is positioned opposite the underside palmar section 126, and the radius section 114 is positioned opposite the stretchable ulnar panel 124. Typically, the U-shaped support sleeve 120, which opens to a patient's forearm ulna, is substantially inelastic (e.g., formed from flexible, low-stretch material) to help stabilize the patient's wrist and hand.

The stretchable ulnar panel 124, which may be cushioned for the patient's comfort, is affixed to both the U-shaped support sleeve's dorsal section 122 and the U-shaped support sleeve's palmar section 126, thereby closing the gap in the U-shaped support sleeve 120 to form the closed wrist-brace sleeve 112. In addition, the stretchable ulnar panel 124 is typically positioned within the gap in the U-shaped support sleeve 120 to define both an outer dorsal strip 123 and an outer palmar strip 127. More specifically, the outer dorsal strip 123 is defined by the stretchable ulnar panel 124 and an adjacent outer edge of the U-shaped support sleeve 120, and the outer palmar strip 127 is defined by the stretchable ulnar panel 124 and an adjacent outer edge of the U-shaped support sleeve 120.

A thumb-tensioning strap 117 extends from the distal end of the U-shaped support sleeve's radius section 114. The thumb-tensioning strap 117 is positioned between the patient's thumb and forefinger, wrapped around the patient's thumb, and then securely and releasably affixed to the U-shaped support sleeve's radius section 114 (e.g., via hook-and-loop fasteners, such as VELCRO-brand fasteners). The thumb-tensioning strap 117 not only helps to position and secure the wrist brace 110 to the patient's wrist and forearm, but also helps to position and secure the support sleeve's radius section 114 against the base of the patient's thumb. Optional padding 118, which is positioned near the thumb-tensioning strap 117, such as upon the U-shaped support sleeve's palmar section 126 and/or the U-shaped support sleeve's radius section 114, provides the patient with enhanced comfort and support. More generally, padding may be applied to the interior surfaces of the closed wrist-brace sleeve 112 to help engage the patient's wrist and hand and to improve patient comfort.

Figure 7:
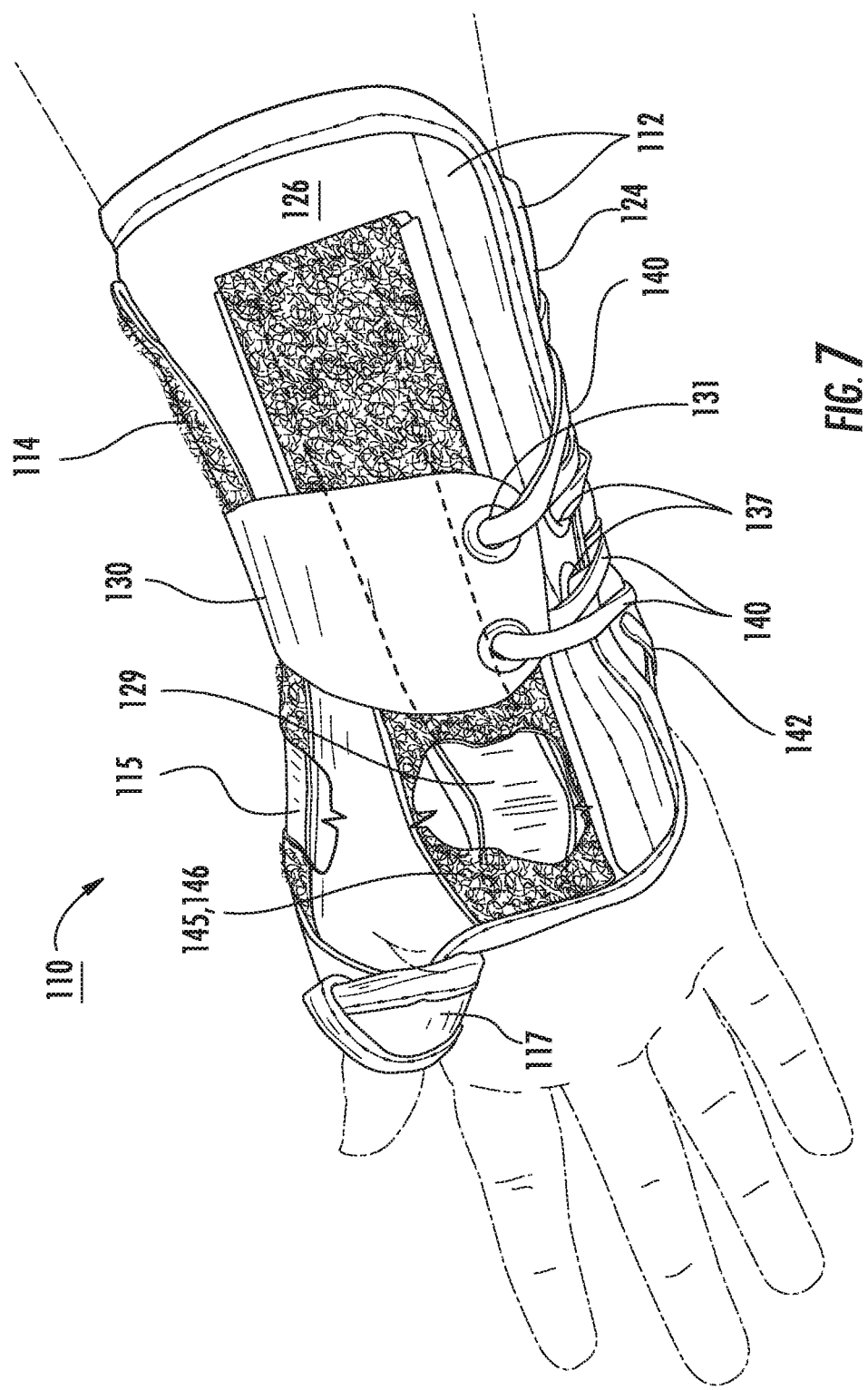
FIGS. 7-10 are perspective views of yet another exemplary wrist-brace embodiment having an advantageous lacing configuration.
Figure 8:
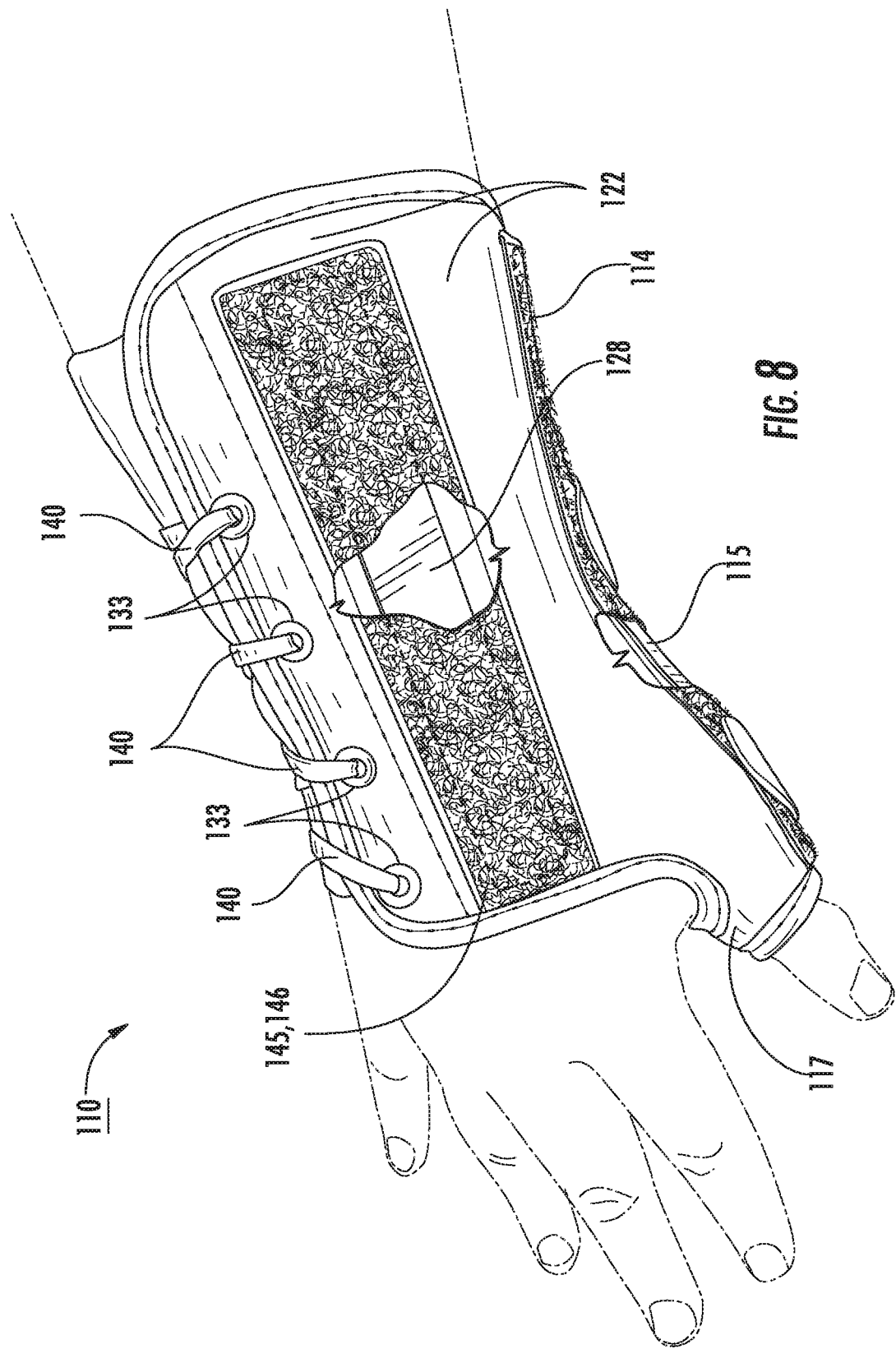

The U-shaped support sleeve 120 can include stabilizing members to limit flexion and extension. In the exemplary wrist-brace embodiments depicted in FIGS. 7-10 and FIGS. 11-12, a longitudinal stiffening dorsal stay 128 is internally secured within the U-shaped support sleeve's dorsal section 122, a longitudinal stiffening radius stay 115 is internally secured within the U-shaped support sleeve's radius section 114, and a longitudinal stiffening palmar stay 129 is internally secured within the U-shaped support sleeve's palmar section 126. As shown in FIGS. 7-8, the radius stay 115 conforms to the shape of the patient's forearm, wrist, and thumb. As shown in FIG. 7, the palmar stay 129 conforms to the shape of the patient's forearm, wrist, and palm. Including stays on two or more sides of the wrist brace (e.g., a wrist brace having a dorsal stay, a radius stay, and a palmar stay,) protects against impact forces and helps reduce the likelihood of reinjuring the patient's wrist and hand.

Dorsal eyelets 133 (or similar openings, such as reinforced holes and/or slots, or other dorsal lace-redirection mechanisms, such as loops, hooks, folded webbing, and/or buckles) are formed through or otherwise positioned at or near (e.g., positioned upon) the U-shaped support sleeve's dorsal section 122 (e.g., at the outer dorsal strip 123). Similarly, palmar eyelets 137 (or similar openings, such as reinforced holes and/or slots, or other palmar lace-redirection mechanisms, such as loops, hooks, folded webbing, and/or buckles) are formed through or otherwise positioned at or near (e.g., positioned upon) the U-shaped support sleeve's palmar section 126 (e.g., at the outer palmar strip 127). The shorter exemplary wrist brace 110 depicted in FIGS. 7-10 includes four dorsal eyelets 133a, 133c, 133f, 133h and two palmar eyelets 137d, 137e (i.e., imbalanced eyelets on either side of the U-shaped support sleeve 120). The longer exemplary wrist brace 110' depicted in FIGS. 11-12 includes six dorsal eyelets 133a, 133c, 133f, 133h, 133k, 133n and four palmar eyelets 137d, 137e, 137i, 137j (i.e., imbalanced eyelets on either side of the U-shaped support sleeve 120). Those having ordinary skill in the art will understand that exemplary wrist braces according to the present invention may employ any lace-redirection mechanisms (e.g., reinforced holes and slots, or external loops, hooks, folded webbing, and/or buckles) in addition to or instead of eyelets.

As noted, it is within the scope of the present wrist-brace invention to include one or more external flaps (not shown) on the exterior of the U-shaped support sleeve to facilitate redirection of the lace. In one wrist-brace embodiment, a dorsal flap having eyelets or other lace-redirection mechanisms can be positioned upon the U-shaped support sleeve's dorsal section (e.g., near the stretchable ulnar panel), and the lace may be guided through the dorsal flap's lace-redirection mechanisms (e.g., eyelets) and the palmar eyelets (or other lace-redirection mechanisms) to promote even closure of the closed wrist-brace sleeve and to achieve cast-like compression on a patient's forearm, wrist, and hand. In another wrist-brace embodiment, a palmar flap having eyelets or other lace-redirection mechanisms can be positioned upon the U-shaped support sleeve's palmar section (e.g., near the stretchable ulnar panel), and the lace may be guided through the palmar flap's lace-redirection mechanisms (e.g., eyelets) and the dorsal eyelets (or other lace-redirection mechanisms) to promote even closure of the closed wrist-brace sleeve and to achieve cast-like compression on a patient's forearm, wrist, and hand. In yet another wrist-brace embodiment, a lace may be guided through both (i) a dorsal flap having eyelets or other lace-redirection mechanisms and (ii) a palmar flap having eyelets or other lace-redirection mechanisms to achieve cast-like compression on a patient's forearm, wrist, and hand, thereby restricting flexion, extension, and lateral movement of the wrist joint.

The shorter exemplary wrist brace 110 depicted in FIGS. 7-10 includes a lacing closure tab 130 through which one or more closure-tab eyelets 131 are formed. The longer exemplary wrist brace 110' depicted in FIGS. 11-12 includes multiple lacing closure tabs 130' and 130" through which one or more closure-tab eyelets 131 are formed. More generally, closure-tab eyelets 131 (or similar openings, such as reinforced holes and/or slots, or other closure-tab lace-redirection mechanisms, such as loops, hooks, folded webbing, and/or buckles) may be formed through or otherwise positioned at or near (e.g., positioned upon) the lacing closure tab(s) 130.

Each lacing closure tab 130 includes a mechanism, such as a hook-and-loop fastener, to releasably secure the lacing closure tab 130 to another part of the wrist brace 110. In the shorter exemplary wrist-brace embodiment depicted in FIG. 9, two closure-tab eyelets 131b, 131g are formed through or otherwise positioned upon the lacing closure tab 130. In the longer exemplary wrist-brace embodiment depicted in FIG. 11, one closure-tab eyelet 131b is formed through or otherwise positioned upon the proximal lacing closure tab 130' and two closure-tab eyelets 131g, 131m are formed through or otherwise positioned upon the distal lacing closure tab 130". The closure-tab eyelets 131 help to ensure that each lacing closure tab 130 remains centered on the U-shaped support sleeve 120 as the lacing closure tab 130 is pulled over and around the closed wrist-brace sleeve 112.

A lace 140 is freely threaded (or otherwise interlaced) though the respective dorsal eyelets 133, palmar eyelets 137, and closure-tab eyelets 131. The lace 140 can move freely to accommodate the typical non-cylindrical anatomy of a patient's forearm in which the arm tapers from the elbow to the wrist (e.g., a frustoconical shape). This free movement of the lace 140 facilitates consistent tension along the lace 140. This even tension is transferred to the respective dorsal eyelets 133, palmar eyelets 137, and closure-tab eyelets 131 through which the lace 140 is interlaced.

Each lacing closure tab 130 is moveably connected to the lace 140. When the lacing closure tab 130 is not releasably secured to another part of the wrist brace (e.g., releasably affixed to the closed wrist-brace sleeve 112), the lacing closure tab 130 can move substantially freely along the lace 140. The shorter exemplary wrist brace 110 depicted in FIGS. 7-10 does not fixedly attach the one lace 140 to the lacing closure tab 130, either fully or partially. Similarly, the longer exemplary wrist brace 110' depicted in FIGS. 11-12 does not fixedly attach the one lace 140 to the respective closure tabs 130' and 130", either fully or partially. Rather, in these exemplary wrist-brace embodiments, the lace 140 may pass substantially freely through each of the closure-tab eyelets 131. As depicted in FIGS. 7-12, each strand of lace 140 from a dorsal eyelet 133 to a closure tab 130 is freely threaded through a closure-tab eyelet 131. This "free-floating" closure-tab design enables the patient to readily equilibrate lace tension through the various eyelets (i.e., the dorsal eyelets 133 and palmar eyelets 137) positioned along the length of the wrist brace in a way that applies substantially consistent compression to the patient's forearm and wrist. The lace 140 and each moveably attached lacing closure tab 130 wrap circumferentially around—rather than helically along—the patient's forearm in a way that uniformly closes and tensions the closed wrist-brace sleeve 112.

Typically, one lace 140 has (i) a first end fixed to the U-shaped support sleeve's interior surface at the U-shaped support sleeve's proximal end (e.g., secured at either the proximal end of the outer palmar strip 127 or the proximal end of the outer dorsal strip 123) and (ii) a second end fixed to the U-shaped support sleeve's interior surface at the U-shaped support sleeve's distal end (e.g., secured at either the distal end of the outer palmar strip 127 or the distal end of the outer dorsal strip 123). In this embodiment, either the dorsal eyelets 133 or the palmar eyelets 137 are positioned between the lace's first fixed end and the lace's second fixed end.

As illustrated in FIGS. 7-10 in which the ends of lace 140 are fixed to the outer palmar strip 127, pulling the lacing closure tab 130 away from the U-shaped support sleeve's dorsal section 122 (and over and around the U-shaped support sleeve's palmar section 126) uniformly closes and tensions the closed wrist-brace sleeve 112 by drawing together the U-shaped support sleeve's dorsal section 122 and the U-shaped support sleeve's palmar section 126. Similarly, in an alternative wrist-brace embodiment in which the ends of lace 40 are fixed to the outer dorsal strip 123, pulling the lacing closure tab away from the U-shaped support sleeve's palmar section 126 (and over and around the U-shaped support sleeve's dorsal section 122) uniformly closes and tensions the closed wrist-brace sleeve 112 by drawing together the U-shaped support sleeve's palmar section 126 and the U-shaped support sleeve's dorsal section 122. These same considerations apply to wrist-brace embodiments that include multiple lacing closure tabs, such as the proximal lacing closure tab 130' and the distal lacing closure tab 130" illustrated in FIGS. 11-12.

Figure 9:
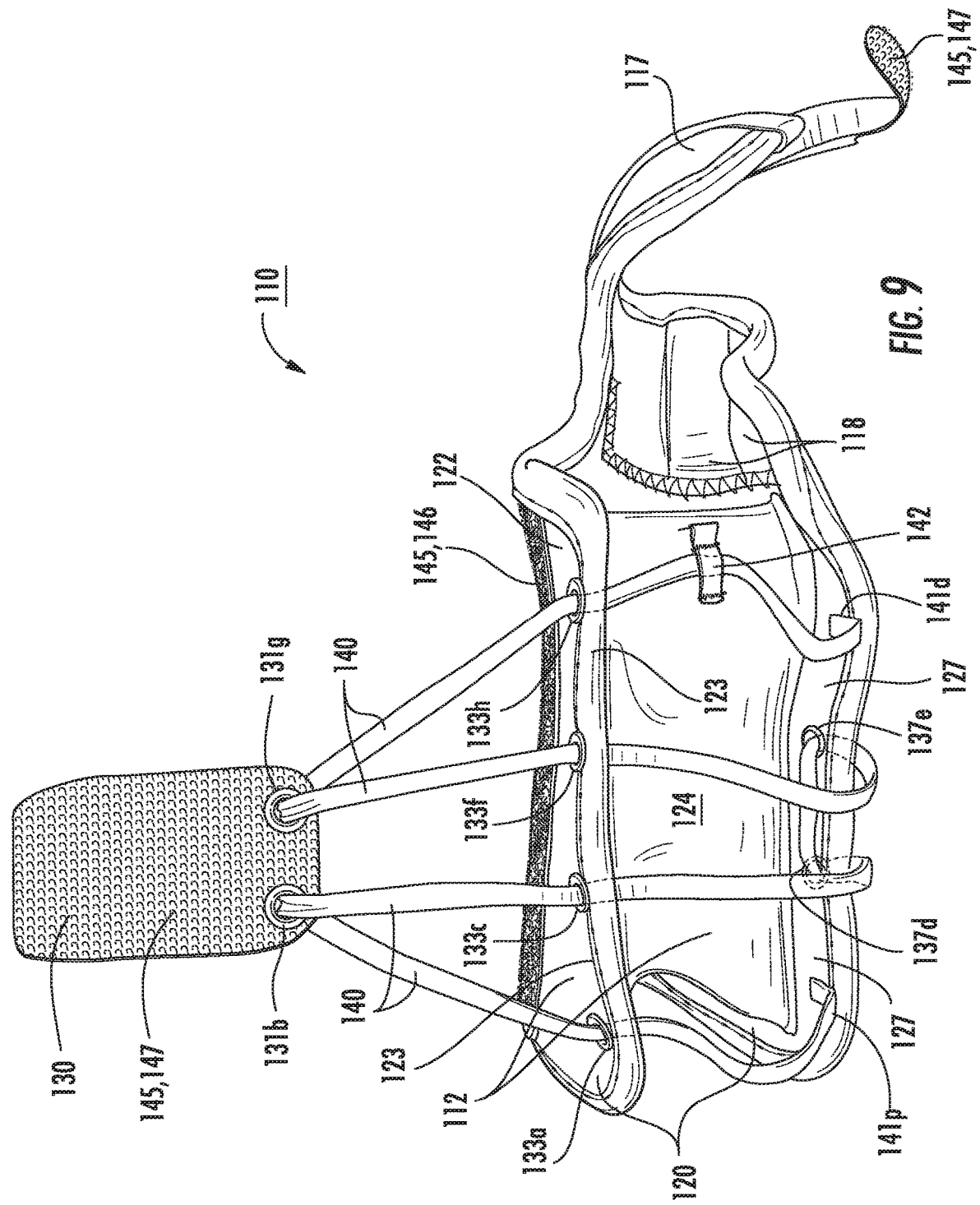
Figure 10:
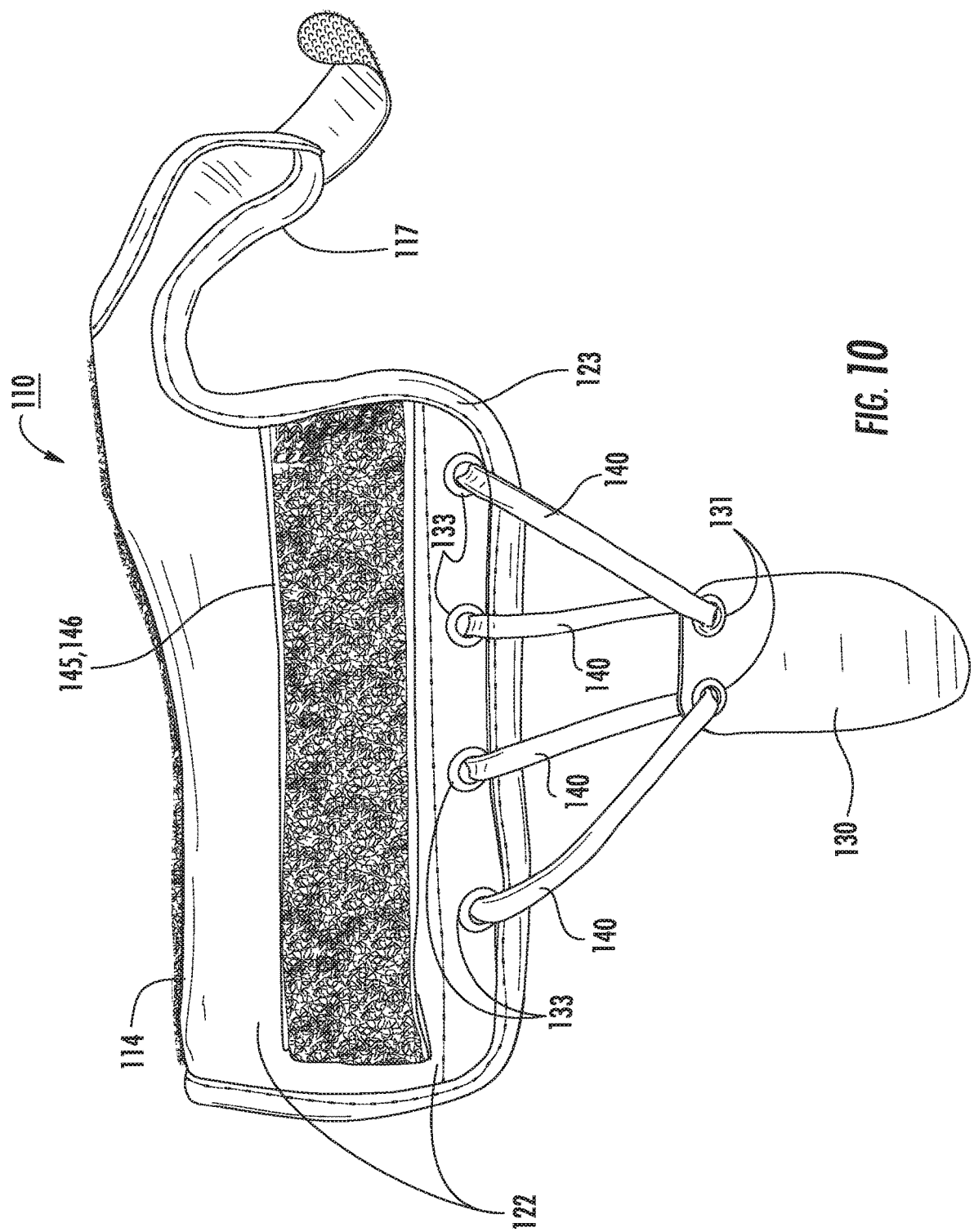

In the shorter exemplary wrist-brace embodiment depicted in FIG. 9, a single lace 140 has (i) a first proximal end fixed to the U-shaped support sleeve's interior surface nearer the U-shaped support sleeve's proximal end (i.e., a proximal fixation 141*p* toward the proximal end of the outer palmar strip 127) and (ii) a second distal end fixed to the U-shaped support sleeve's interior surface nearer the U-shaped support sleeve's distal end (i.e., a distal fixation 141*d* toward the distal end of the outer palmar strip 127). In the exemplary wrist-brace embodiment depicted in FIG. 9, two palmar eyelets 137*d*, 137*e* are formed along outer palmar strip 127 between the lace's proximal fixation 141*p* and the lace's distal fixation 141*d*, and four dorsal eyelets 133*a*, 133*c*, 133*f*, 137*h* are formed along the outer dorsal strip 123.

As illustrated in the exemplary wrist-brace embodiment depicted in FIG. 9, the wrist brace 110 includes a compression-enhancing lacing configuration that readily equilibrates (e.g., simultaneously evens) the tension in the lace 140 as the lacing closure tab 130 is extended from the closed wrist-brace sleeve 112. From the proximal end of the wrist brace 110 to the distal end of the wrist brace 110, the lace 140 passes from its proximal fixation 141*p* to and through an outer proximal dorsal eyelet 133*a*, to and through a proximal closure-tab eyelet 131*b*, to and through an inner proximal dorsal eyelet 133*c*, to and through a proximal palmar eyelet 137*d*. The lace 140 then passes lengthwise along the interior surface of the outer palmar strip 127 from the proximal palmar eyelet 137*d* to and through a distal palmar eyelet 137*e* so that, between the proximal palmar eyelet 137*d* and the distal palmar eyelet 137*e*, the lace 140 is substantially parallel to the adjacent outer edge of the U-shaped support sleeve 120. The lace 140 then passes from the distal palmar eyelet 137*e* to and through an inner distal dorsal eyelet 133*f*, to and through a distal closure-tab eyelet 131*g*, to and through an outer distal dorsal eyelet 133*h*, and to the distal fixation 141*d*.

In the longer exemplary wrist-brace embodiment depicted in FIG. 11, a single lace 140 has (i) a first proximal end fixed to the U-shaped support sleeve's interior surface nearer the U-shaped support sleeve's proximal end (i.e., a proximal fixation 141*p* toward the proximal end of the outer palmar strip 127) and (ii) a second distal end fixed to the U-shaped support sleeve's interior surface nearer the U-shaped support sleeve's distal end (i.e., a distal fixation 141*d* toward the distal end of the outer palmar strip 127). In the exemplary wrist-brace embodiment depicted in FIG. 11, four palmar eyelets 137*d*, 137*e*, 137*i*, 137*j* are formed along outer palmar strip 127 between the lace's proximal fixation 141*p* and the lace's distal fixation 141*d*, and six dorsal eyelets 133*a*, 133*c*, 133*f*, 133*h*, 133*k*, 133*n* are formed along the outer dorsal strip 123.

As illustrated in the exemplary wrist-brace embodiment depicted in FIG. 11, the wrist brace 110' includes a compression-enhancing lacing configuration that readily equilibrates the tension in the lace 140 as the lacing closure tabs 130', 130" are extended from the closed wrist-brace sleeve 112. From the proximal end of the wrist brace 110' to the distal end of the wrist brace 110', the lace 140 passes from its proximal fixation 141*p* to and through an outermost proximal dorsal eyelet 133*a*, to and through a closure-tab eyelet 131*b* formed in the proximal lacing closure tab 130', to and through a central proximal dorsal eyelet 133*c*, to and through an outer proximal palmar eyelet 137*d*. The lace 140 then passes lengthwise along the interior surface of the outer palmar strip 127 from the outer proximal palmar eyelet 137*d* to and through an inner proximal palmar eyelet 137*e* so that, between the outer proximal palmar eyelet 137*d* and the inner proximal palmar eyelet 137*e*, the lace 140 is substantially parallel to the adjacent outer edge of the U-shaped support sleeve 120. The lace 140 then passes from the inner proximal palmar eyelet 137*e* to and through an inner proximal dorsal eyelet 133*f*, to and through a first distal closure-tab eyelet 131*g* formed in the distal lacing closure tab 130", to and through an inner distal dorsal eyelet 133*h*, to and through an inner distal palmar eyelet 137*i*. The lace 140 then passes lengthwise along the interior surface of the outer palmar strip 127 from the inner distal palmar eyelet 137*i* to and through an outer distal palmar eyelet 137*j* so that, between the inner distal palmar eyelet 137*i* and the outer distal palmar eyelet 137*j*, the lace 140 is substantially parallel to the adjacent outer edge of the U-shaped support sleeve 120. The lace 140 then passes from the outer distal palmar eyelet 137*j* to and through a central distal dorsal eyelet 133*k*, to and through a second distal closure-tab eyelet 131*m* formed in the distal lacing closure tab 130", to and through an outermost distal dorsal eyelet 133*n*, and to the distal fixation 141*d*.

Optionally, the lace 140 passes through one or more lacing channels 142, which may be secured to or otherwise formed in the stretchable ulnar panel 124. In the shorter exemplary wrist-brace embodiment depicted in FIG. 9, the lace 140 passes through one lacing channel 142 secured to the stretchable ulnar panel 124 as the lace 140 passes from the outer distal dorsal eyelet 133*h* to the distal fixation 141*d*. In the longer exemplary wrist-brace embodiment depicted in FIG. 11, the lace 140 passes through one lacing channel 142 secured to the stretchable ulnar panel 124 as the lace 140 passes from the outermost distal dorsal eyelet 133*n* to the distal fixation 141*d*. As will be appreciated by those having ordinary skill in the art, each lacing channel 142 should be positioned to facilitate passage of the lace 140 between the outer palmar strip 127 and the outer dorsal strip 123. For example, positioning lacing channel(s) 142 at either the distal end or the proximal end of the stretchable ulnar panel 124, or both the distal end and the proximal end of the stretchable ulnar panel 124, helps to maintain the proper positioning of stretchable ulnar panel 124 against the patient's forearm as shown in FIG. 8. In practice, securing the lace 140 to the stretchable ulnar panel 124 via one or more lacing channels 142, typically at the distal end and/or proximal end of a cushioned, stretchable ulnar panel 124, reduces patient discomfort by preventing the lace 140 from migrating beyond the end of the stretchable ulnar panel 124 when the wrist brace 110 is compressively and securely applied to the patient's wrist and forearm.

As illustrated in the exemplary wrist-brace embodiments depicted in FIGS. 7-10 and FIGS. 11-12, hook-and-loop fasteners 145 are secured to the surfaces of the wrist brace 110 to facilitate closure of the wrist brace 110 to the patient's forearm, wrist, and hand. For example, loop-fasteners 146 (e.g., loop-fastener strips) can be secured to the outer surfaces of the U-shaped support sleeve 120, typically at the topside dorsal section 122, the radius section 114, and the underside palmar section 126. Hook-fasteners 147 are provided elsewhere on the wrist brace 110, such as on a surface of each lacing closure tab 130 and a surface at the end of the thumb-tensioning strap 117.

As illustrated in FIGS. 7-10 and FIGS. 11-12, the patient may secure the wrist brace 110 to his forearm, wrist, and hand by pulling a lacing closure tab 130 perpendicularly away from the U-shaped support sleeve's dorsal section 122 and over and around the U-shaped support sleeve's palmar section 126. This evenly closes and tensions the closed wrist-brace sleeve 112 by drawing together the U-shaped support sleeve's dorsal section 122 and the U-shaped support sleeve's palmar section 126. Depending on the girth of the patient's forearm, the hook-fasteners 147 on a surface of the lacing closure tab 130 will engage one or more loop-fasteners 146 positioned upon the respective outer surfaces of the dorsal section 122, the radius section 114, and the palmar section 126. The hook-fastener 147 at the end of the thumb-tensioning strap 117 can be releasably secured to either the U-shaped support sleeve's radius section 114 or U-shaped support sleeve's palmar section 126.

To supplement the present disclosure, this application incorporates entirely by reference the following commonly assigned patent applications: U.S. Patent Application No. 62/257,941 for a Universal Wrist Brace with Enhanced Lacing (filed Nov. 20, 2015); U.S. Patent Application No. 62/400,382 for a Universal Wrist Brace with Enhanced Lacing (filed Sep. 27, 2016); and U.S. patent application Ser. No. 15/355,587 for a Universal Wrist Brace with Enhanced Lacing (concurrently filed Nov. 18, 2016).

In the specification and/or figures, typical embodiments of the wrist-brace invention have been disclosed. The present wrist-brace invention is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The invention claimed is:

1. A wrist brace, comprising:
a U-shaped support sleeve having a dorsal section, an ulnar section, and a palmar section, wherein the ulnar section is contiguously positioned between the dorsal section and the palmar section;
a radius panel connecting the U-shaped support sleeve's dorsal section and the U-shaped support sleeve's palmar section, the radius panel being affixed to the U-shaped support sleeve such that together the U-shaped support sleeve and radius panel form a closed wrist-brace sleeve;
dorsal lace-redirection mechanisms positioned at or near the U-shaped support sleeve's dorsal section;
palmar lace-redirection mechanisms positioned at or near the U-shaped support sleeve's palmar section;
a lacing closure tab having one or more closure-tab lace-redirection mechanisms;
a lace having (i) a first end fixed to the U-shaped support sleeve nearer a proximal end of the U-shaped support sleeve and (ii) a second end fixed to the U-shaped support sleeve nearer a distal end of the U-shaped support sleeve, wherein the lace has (i) its first end fixedly connected to the U-shaped support sleeve's palmar section near a proximal end of the palmar section and (ii) its second end fixedly connected to the U-shaped support sleeve's palmar section near a distal end of the palmar section, and wherein the lace is freely threaded though the respective dorsal lace-redirection mechanisms, palmar lace-redirection mechanisms, and closure-tab lace-redirection mechanisms; and
an oblique palmar-tensioning strap that extends from the distal end of the U-shaped support sleeve's palmar section, wherein the oblique palmar-tensioning strap is configured to be positioned between a patient's thumb and forefinger and to be releasably affixed to the U-shaped support sleeve when the wrist brace is secured to the patient's wrist and forearm;
wherein the palmar-tensioning strap and the lacing closure tab are configured to be oppositely circumferentially wrapped around the wrist-brace sleeve from one another when the wrist brace is secured to the patient's wrist and forearm.

2. The wrist brace according to claim 1, wherein:
the lacing closure tab having one or more closure-tab lace-redirection mechanisms is a first lacing closure tab having one or more first closure-tab lace-redirection mechanisms;
the wrist brace comprises a second lacing closure tab having one or more second closure-tab lace-redirection mechanisms; and
the lace is freely threaded though the respective dorsal lace-redirection mechanisms, palmar lace-redirection mechanisms, first closure-tab lace-redirection mechanisms, and second closure-tab lace-redirection mechanisms.

3. The wrist brace according to claim 1, wherein:
a lengthwise direction of the U-shaped support sleeve extends from the U-shaped support sleeve's proximal end to the U-shaped support sleeve's distal end; and
in the lengthwise direction of the U-shaped support sleeve, the palmar lace-redirection mechanisms are positioned between the lace's first end and the lace's second end.

4. The wrist brace according to claim 1, wherein:
the dorsal lace-redirection mechanisms comprise dorsal eyelets positioned in an outer dorsal strip of the U-shaped support sleeve's dorsal section, the outer dorsal strip is defined between the radius panel and an adjacent outer edge of the U-shaped support sleeve's dorsal section; and/or
the palmar lace-redirection mechanisms comprise palmar eyelets positioned in an outer palmar strip of the U-shaped support sleeve's palmar section, the outer palmar strip is defined between the radius panel and an adjacent outer edge of the U-shaped support sleeve's palmar section; and/or the closure-tab lace-redirection mechanisms comprise closure-tab eyelets positioned on the lacing closure tab.

5. The wrist brace according to claim 1, comprising a lacing channel secured to the radius panel, wherein the lace is freely threaded through the lacing channel.

6. The wrist brace according to claim 1, wherein the lacing closure tab is configured to be releasably affixed to the U-shaped support sleeve when the wrist brace is secured to a patient's wrist and forearm.

7. The wrist brace according to claim 1, wherein the wrist brace is configured to provide a consistent, cast-like compression of the wrist brace to the patient's forearm and wrist in response to (i) pulling the lacing closure tab and the attached lace away from the patient's forearm and then (ii) wrapping the lacing closure tab and the attached lace around the wrist-brace sleeve.

8. The wrist brace according to claim 7, wherein exactly one lace moveably connects the wrist-brace sleeve and the lacing closure tab.

9. The wrist brace according to claim 1, wherein:
the palmar lace-redirection mechanisms comprise palmar eyelets positioned in an outer palmar strip of the U-shaped support sleeve's palmar section, the outer palmar strip is defined between the radius panel and an adjacent outer edge of the U-shaped support sleeve's palmar section;
between the palmar eyelets, a section of the lace extends along and parallel to the adjacent outer edge of the U-shaped support sleeve's palmar section; and
the lace has (i) its first end fixedly connected to the outer palmar strip and (ii) its second end fixedly connected to the outer palmar strip.

10. The wrist brace according to claim 9, wherein:
the section of the lace is directly next to an inner surface the outer palmar strip; and
the lace has (i) its first end fixedly connected to the inner surface the outer palmar strip and (ii) its second end fixedly connected to the inner surface of the outer palmar strip.

11. The wrist brace according to claim 1, wherein:
the dorsal lace-redirection mechanisms comprise dorsal eyelets positioned in an outer dorsal strip of the U-shaped support sleeve's dorsal section, the outer dorsal strip is defined between the radius panel and an adjacent outer edge of the U-shaped support sleeve's dorsal section;
the palmar lace-redirection mechanisms comprise palmar eyelets positioned in an outer palmar strip of the U-shaped support sleeve's palmar section, the outer palmar strip is defined between the radius panel and an adjacent outer edge of the U-shaped support sleeve's palmar section; and
the closure-tab lace-redirection mechanisms comprise closure-tab eyelets positioned on the lacing closure tab.

12. The wrist brace according to claim 1, wherein in a direction along the lace from the lace's first end to the lace's second end:
the lace extends from the lace's first end to and through an outer proximal dorsal eyelet of the dorsal lace-redirection mechanisms;
then the lace extends from the outer proximal dorsal eyelet to and through a proximal closure-tab eyelet of the closure-tab lace-redirection mechanisms;

then the lace extends from the proximal closure-tab eyelet to and through an inner proximal dorsal eyelet of the dorsal lace-redirection mechanisms;
then the lace extends from the inner proximal dorsal eyelet to and through a proximal palmar eyelet of the palmar lace-redirection mechanisms;
then the lace extends from the proximal palmar eyelet of the palmar lace-redirection mechanisms lengthwise along an interior surface of an outer palmar strip of the U-shaped support sleeve to and through a distal palmar eyelet of the palmar lace-redirection mechanisms so that, between the proximal palmar eyelet and the distal palmar eyelet, the lace extends along an adjacent outer edge of the U-shaped support sleeve's palmar section, and the outer palmar strip is defined between the radius panel and the adjacent outer edge of the U-shaped support sleeve's palmar section;
then the lace extends from the distal palmar eyelet to and through an inner distal dorsal eyelet of the dorsal lace-redirection mechanisms;
then the lace extends from the inner distal dorsal eyelet to and through a distal closure-tab eyelet of the closure-tab lace-redirection mechanisms;
then the lace extends from the distal closure-tab eyelet to and through an outer distal dorsal eyelet of the dorsal lace-redirection mechanisms; and
then the lace extends from the outer distal dorsal eyelet to the lace's second end.

13. The wrist brace according to claim 12, comprising a lacing channel secured to the radius panel, wherein:
the lace is freely threaded through the lacing channel;
the lace extends from the outer distal dorsal eyelet to and through the lacing channel; and
then the lace extends from the lacing channel to the lace's second end.

14. The wrist brace according to claim 1, wherein:
the palmar-tensioning strap is configured to be releasably affixed to the U-shaped support sleeve's dorsal section when the wrist brace is secured to the patient's wrist and forearm; and
the lacing closure tab is configured to be releasably affixed to the U-shaped support sleeve's ulnar section when the wrist brace is secured to the patient's wrist and forearm.

15. A wrist brace, comprising:
a U-shaped support sleeve having a dorsal section, an ulnar section, and a palmar section, wherein the ulnar section is contiguously positioned between the dorsal section and the palmar section;
a radius panel connecting the U-shaped support sleeve's dorsal section and the U-shaped support sleeve's palmar section, the radius panel being affixed to the U-shaped support sleeve such that together the U-shaped support sleeve and radius panel form a closed wrist-brace sleeve;
dorsal lace-redirection mechanisms positioned at or near the U-shaped support sleeve's dorsal section;
palmar lace-redirection mechanisms positioned at or near the U-shaped support sleeve's palmar section;
a lacing closure tab having one or more closure-tab lace-redirection mechanisms;
a lace having (i) a first end fixedly connected to the U-shaped support sleeve's palmar section and (ii) a second end fixedly connected to the U-shaped support sleeve's palmar section, and wherein, in a direction along a length of the palmar section, the palmar lace-redirection mechanisms are positioned between the lace's first end and the lace's second end.

16. The wrist brace according to claim 15, comprising a lacing channel secured to the radius panel, wherein the lace is freely threaded through the lacing channel.

17. The wrist brace according to claim 15, wherein:
a lengthwise direction of the U-shaped support sleeve extends from the U-shaped support sleeve's proximal end to the U-shaped support sleeve's distal end; and
in the lengthwise direction of the U-shaped support sleeve, the palmar lace-redirection mechanisms are positioned between the lace's first end and the lace's second end.

18. The wrist brace according to claim 15, wherein the lacing closure tab is configured to be releasably affixed to the U-shaped support sleeve when the wrist brace is secured to a patient's wrist and forearm.

19. The wrist brace according to claim 15, wherein:
the palmar lace-redirection mechanisms comprise palmar eyelets positioned in an outer palmar strip of the U-shaped support sleeve's palmar section, the outer palmar strip is defined between the radius panel and an adjacent outer edge of the U-shaped support sleeve's palmar section; and
the lace has (i) its first end fixedly connected to the outer palmar strip and (ii) its second end fixedly connected to the outer palmar strip.

20. The wrist brace according to claim 19, wherein in a direction along the lace from the lace's first end to the lace's second end:
the lace extends from the lace's first end to and through an outer proximal dorsal eyelet of the dorsal lace-redirection mechanisms;
then the lace extends from the outer proximal dorsal eyelet to and through a proximal closure-tab eyelet of the closure-tab lace-redirection mechanisms;
then the lace extends from the proximal closure-tab eyelet to and through an inner proximal dorsal eyelet of the dorsal lace-redirection mechanisms;
then the lace extends from the inner proximal dorsal eyelet to and through a proximal palmar eyelet of the palmar eyelets;
then the lace extends from the proximal palmar eyelet of the palmar eyelets lengthwise along an interior surface of an outer palmar strip of the U-shaped support sleeve to and through a distal palmar eyelet of the palmar eyelets so that, between the proximal palmar eyelet and the distal palmar eyelet, the lace extends along an adjacent outer edge of the U-shaped support sleeve's palmar section, and the outer palmar strip is defined between the radius panel and the adjacent outer edge of the U-shaped support sleeve's palmar section;
then the lace extends from the distal palmar eyelet to and through an inner distal dorsal eyelet of the dorsal lace-redirection mechanisms;
then the lace extends from the inner distal dorsal eyelet to and through a distal closure-tab eyelet of the closure-tab lace-redirection mechanisms;
then the lace extends from the distal closure-tab eyelet to and through an outer distal dorsal eyelet of the dorsal lace-redirection mechanisms; and
then the lace extends from the outer distal dorsal eyelet to the lace's second end.

21. The wrist brace according to claim 20, comprising a lacing channel secured to the radius panel, wherein:
the lace is freely threaded through the lacing channel;
the lace extends from the outer distal dorsal eyelet to and through the lacing channel; and
then the lace extends from the lacing channel to the lace's second end.

22. The wrist brace according to claim 19, wherein the lace has (i) its first end fixedly connected to an inner surface the outer palmar strip and (ii) its second end fixedly connected to the inner surface of the outer palmar strip.

23. The wrist brace according to claim 15, wherein:
the palmar-tensioning strap is configured to be releasably affixed to the U-shaped support sleeve's dorsal section when the wrist brace is secured to the patient's wrist and forearm; and
the lacing closure tab is configured to be releasably affixed to the U-shaped support sleeve's ulnar section when the wrist brace is secured to the patient's wrist and forearm.

* * * * *